(12) United States Patent
Wipf et al.

(10) Patent No.: US 9,532,999 B2
(45) Date of Patent: *Jan. 3, 2017

(54) TLR4 INHIBITORS FOR THE TREATMENT OF HUMAN INFECTIOUS AND INFLAMMATORY DISORDERS

(71) Applicant: University of Pittsburgh—of the Commonwealth System of Higher Education, Pittsburgh, PA (US)

(72) Inventors: Peter Wipf, Pittsburgh, PA (US); Matthew D. Neal, Pittsburgh, PA (US); Sodhi P. Chhinder, Sewickley, PA (US); David J. Hackam, Pittsburgh, PA (US)

(73) Assignee: UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/717,349

(22) Filed: May 20, 2015

(65) Prior Publication Data

US 2015/0250809 A1 Sep. 10, 2015

Related U.S. Application Data

(63) Continuation of application No. 13/848,809, filed on Mar. 22, 2013, now Pat. No. 9,072,760, which is a continuation of application No. PCT/US2011/053293, filed on Sep. 26, 2011.

(60) Provisional application No. 61/386,345, filed on Sep. 24, 2010, provisional application No. 61/387,335, filed on Sep. 28, 2010.

(51) Int. Cl.
| | |
|---|---|
| *A01N 43/04* | (2006.01) |
| *A61K 31/70* | (2006.01) |
| *A61K 31/7024* | (2006.01) |
| *A61K 31/7008* | (2006.01) |
| *A61K 31/7034* | (2006.01) |
| *A61K 31/7028* | (2006.01) |

(52) U.S. Cl.
CPC ....... *A61K 31/7024* (2013.01); *A61K 31/7008* (2013.01); *A61K 31/7028* (2013.01); *A61K 31/7034* (2013.01)

(58) Field of Classification Search
None
See application file for complete search history.

(56) References Cited

U.S. PATENT DOCUMENTS

| | | | |
|---|---|---|---|
| 4,357,322 A | 11/1982 | Rooks et al. | |
| 5,506,204 A | 4/1996 | Aston | |
| 5,756,718 A | 5/1998 | Christ et al. | |
| 6,214,806 B1 | 4/2001 | Krieg et al. | |
| 6,613,751 B2 | 9/2003 | Raz et al. | |
| 7,038,029 B2 | 5/2006 | Lopez | |
| 7,049,302 B1 | 5/2006 | Kensil | |
| 7,129,222 B2 | 10/2006 | Van Nest et al. | |
| 7,183,111 B2 | 2/2007 | Van Nest et al. | |
| 7,250,397 B2 | 7/2007 | Larsen et al. | |
| 7,348,316 B2 | 3/2008 | Rossignol et al. | |
| 7,744,884 B2 | 6/2010 | Elson | |
| 8,188,058 B2 | 5/2012 | Hackam et al. | |
| 8,518,903 B2 | 8/2013 | Hackam | |
| 8,518,905 B2 | 8/2013 | Hackam et al. | |
| 9,072,760 B2 | 7/2015 | Wipf et al. | |
| 2006/0211752 A1 | 9/2006 | Kohn et al. | |
| 2006/0241040 A1 | 10/2006 | Visintin et al. | |
| 2007/0004654 A1 | 1/2007 | Raz et al. | |
| 2008/0311112 A1 | 12/2008 | Hackam et al. | |
| 2009/0010902 A1 | 1/2009 | Masuda | |
| 2013/0345154 A1 | 12/2013 | Hackam | |
| 2014/0086982 A1 | 3/2014 | Hackam | |
| 2015/0056217 A1 | 2/2015 | Hackam | |

FOREIGN PATENT DOCUMENTS

| | | |
|---|---|---|
| JP | 01-180894 | 7/1989 |
| WO | WO 00/61555 A1 | 10/2000 |
| WO | WO 2004/096156 | 11/2004 |
| WO | WO 2006/092049 A1 | 9/2006 |
| WO | WO 2007/106886 A2 | 9/2007 |
| WO | WO 2007/120368 | 10/2007 |

OTHER PUBLICATIONS

U.S. Appl. No. 12/104,816, May 14, 2013 Certificate of Correction.
U.S. Appl. No. 12/104,816, Apr. 23, 2012 Issue Fee payment.
U.S. Appl. No. 12/104,816, Jan. 23, 2012 Notice of Allowance.
U.S. Appl. No. 12/104,816, Nov. 10, 2011 Amendment and Request for Continued Examination (RCE).
U.S. Appl. No. 12/104,816, May 10, 2011 Final Office Action.
U.S. Appl. No. 12/104,816, Feb. 24, 2011 Response to Non-Final Office Action.
U.S. Appl. No. 12/104,816, Nov. 24, 2010 Non-Final Office Action.
U.S. Appl. No. 12/104,816, Sep. 15, 2010 Response to Restriction Requirement.
U.S. Appl. No. 12/104,816, Aug. 9, 2010 Restriction Requirement.
U.S. Appl. No. 13/068,553, Jul. 25, 2013 Issue Fee payment.
U.S. Appl. No. 13/068,553, Apr. 30, 2013 Notice of Allowance.
U.S. Appl. No. 13/068,553, Apr. 12, 2013 Response to Non-Final Office Action.

(Continued)

*Primary Examiner* — Patrick Lewis
(74) *Attorney, Agent, or Firm* — Baker Botts L.L.P.

(57) ABSTRACT

The present invention relates to methods of treating infectious, inflammatory and post-traumatic disorders by administering various compounds newly discovered to have TLR4 inhibitory activity. In addition to methods of treatment, the present invention further provides for pharmaceutical compositions comprising said compounds, together with a suitable pharmaceutical carrier. Because TLR4 is the most upstream receptor in the pro-inflammatory LPS signaling cascade, treatments of the invention, which inhibit or antagonize TLR4 action, may avoid the pitfalls associated with other cytokine inhibitors that act further down the pathway and accordingly play a less specific (and perhaps non-critical) role.

13 Claims, 19 Drawing Sheets

(56) References Cited

OTHER PUBLICATIONS

Figure 3A:
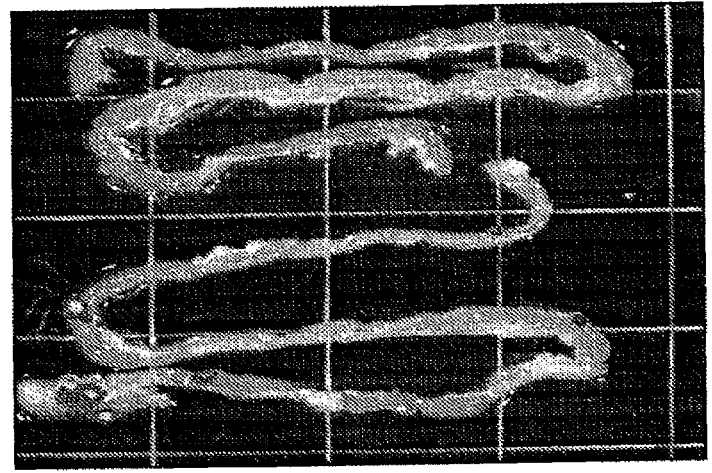

U.S. Appl. No. 13/068,553, Jan. 15, 2013 Non-Final Office Action.
U.S. Appl. No. 13/461,672, Jul. 25, 2013 Issue Fee payment.
U.S. Appl. No. 13/461,672, Apr. 29, 2013 Notice of Allowance.
U.S. Appl. No. 13/461,672, Apr. 12, 2013 Response to Non-Final Office Action.
U.S. Appl. No. 13/461,672, Jan. 14, 2013 Non-Final Office Action.
U.S. Appl. No. 13/848,809, May 12, 2015 Issue Fee Payment.
U.S. Appl. No. 13/848,809, Feb. 17, 2015 Notice of Allowance.
U.S. Appl. No. 13/848,809, Feb. 3, 2015 Request for Continued Examination (RCE).
U.S. Appl. No. 13/848,809, Nov. 10, 2014 Notice of Allowance.
U.S. Appl. No. 13/921,865, Jan. 25, 2016 Non-Final Office Action.
U.S. Appl. No. 13/921,865, Aug. 11, 2015 Amendment and Request for Continued Examination (RCE).
U.S. Appl. No. 13/921,865, Mar. 11, 2015 Final Office Action.
U.S. Appl. No. 13/921,865, Nov. 14, 2014 Response to Non-Final Office Action.
U.S. Appl. No. 13/921,865, Aug. 14, 2014 Non-Final Office Action.
U.S. Appl. No. 13/921,865, Jul. 10, 2014 Response to Non-Final Office Action.
U.S. Appl. No. 13/921,865, Mar. 12, 2014 Non-Final Office Action.
U.S. Appl. No. 13/921,865, Nov. 27, 2013 Response to Restriction Requirement.
U.S. Appl. No. 13/921,865, Sep. 27, 2013 Restriction Requirement.
U.S. Appl. No. 14/036,960, Jan. 4, 2016 Response to Non-Final Office Action.
U.S. Appl. No. 14/036,960, Oct. 1, 2015 Non-Final Office Action.
U.S. Appl. No. 14/036,960, Jul. 9, 2015 Response to Non-Final Office Action.
U.S. Appl. No. 14/036,960, Jan. 12, 2015 Non-Final Office Action.
U.S. Appl. No. 14/036,960, Dec. 22, 2014 Response to Restriction Requirement.
U.S. Appl. No. 14/036,960, Sep. 23, 2014 Restriction Requirement.
U.S. Appl. No. 14/010,232, Sep. 21, 2015 Response to Non-Final Office Action.
U.S. Appl. No. 14/010,232, Jun. 19, 2015 Non-Final Office Action.
U.S. Appl. No. 14/010,232, May 27, 2015 Response to Restriction Requirement.
U.S. Appl. No. 14/010,232, Feb. 27, 2015 Restriction Requirement.
Abreu et al., 2005, "TLR Signaling in the Gut in Health and Disease." J Immunol 174:4453-4460.
Achkar, "Ulcerative colitis: Responding to the challenges", *Cleveland Clinic J. Med.*, 2007; 74(9):657-660.
Afrazi et al. "New insights into the pathogenesis and treatment of necrotizing enterocolitis: Toll-like receptors and beyond", *Pediatr Res.*, 2011; 69:183-188.
Afrazi et al., "Intracellular heat shock protein-70 negatively regulates TLR4 signaling in the newborn intestinal epithelium", *J. Immunol.*, 2012, 188:4543-4557.
Aki Tsukioka, "Eisai Successfully Completes Phase II Trial of Eritoran, Drug Candidate for Severe Sepsis." JCN Network, Aug. 30, 2005 p. 1. Downloaded on Nov. 20, 2009 from http://www.japancorp.net/printarticle.asp?Art_ID=10765.
Amer et al., "Platelet-activating factor concentration in the stool of human newborns: effects of enteral feeding and neonatal necrotizing enterocolitis", *Biol Neonate*, 2004; 85:159-166.
Anand et al., 2007, "The Role of the Intestinal Barrier in the Pathogenesis of Necrotizing Enterocolitis." Shock 27:124-133.
Anderson, 2001, "Infant, neonatal, and postnatal deaths, percent of total deaths, and mortality rates for the 10 leading causes of infant death by race and sex: United States: 1999." National Vital Statistics Reports. 49:73.
Blakely et al., "Postoperative outcomes of extremely low birthweight infants with necrotizing enterocolitis or isolated intestinal perforation: a prospective cohort study by the NICHD Neonatal Research Network", *Ann Surg*. 2005; 241(6):984-989.
Borges et al., "Immune response by nasal delivery of hepatitis B surface and antigen and codelivery of a CpG ODN in alginate coated chitosan nanoparticles", *European Journal of Pharmaceutics and Biopharmaceutics*, 59:405-416 (2008).
Borzutzky et al., "NOD2-associated diseases: Bridging innate immunity and autoinflammation", *Clin Immunol.*, 2010; 134:251-261.
Caplan et al., "Neonatal necrotizing enterocolitis: possible role of probiotic supplementation", *Journal of Pediatric Gastroenterology and Nutrition*, 30(2):S18-S22 (2000).
Caplan et al., "The platelet activating factor receptor antagonist WEB 2170 prevents neonatal necrotizing enterocolitis in rats", *J Pediatr Gastroenterol Nutr.* 1997; 24:296-301.
Caplan et al., "The role of recombinant platelet activating factor acetylhydrolase in a neonatal rat model of necrotizing enterocolitis", *Pediatr Res.*, 1997; 42:779-783.
Caradonna et al., "Phagocytosis, killing, lymphocyte-mediated antibacterial activity, serum autoantibodies, and plasma endotoxins in inflammatory bowel disease", *Am J Gastroenterol*. 2000; 95:1495-1502.
Career Opportunities—Eisai announces Phase II results, plans to initiate phase III clinical—Aug. 29, 2005. Downloaded on Apr. 18, 2007 from http://www.eisai.com/view_pressrelease.asp?ID=145&press=124.
Cario et al., 2000, "Lipopolysaccharide activates distinct signaling pathways in intestinal epithelial cell lines expressing Toll-like receptors." J Immunol. 164(2):966-72.
Carneiro et al., 2008, "Nod-like proteins in inflammation and disease." J Pathol. 214(2):136-48.
Cavallo et al., 2006 "The expression and function of enterocyte toll like receptor-4 are enhanced by lipopolysaccharide in vitro and during systemic endotoxemia." Association for academic surgery and society of university surgeons—Abstracts. Journal of Surgical Researchvol. 130, Issue 2, p. 232, No. 189.
Cetin et al., 2004, "Endotoxin inhibits intestinal epithelial restitution through activation of Rho-GTPase and increased focal adhesions." J Biol Chem. 279(23):24592-600. Epub Mar. 30, 2004.
Cetin et al., 2007, "Nitric oxide inhibits enterocyte migration through activation of RhoA-GTPase in a SHP-2-dependent manner." Am J Physiol Gastrointest Liver Physiol 292:G1347-1358.
Chan et al., "Role of LPS/CD14/TLR4-mediated inflammation in necrotizing enterocolitis: pathogenesis and therapeutic implications", *World J Gastroenterol.*, 2009; 15:4745-4752.
Cho et al., 2007, "The genetics of inflammatory bowel disease." Gastroenterology 133:1327-1339.
Creagh et al., 2006, "TLRs, NLRs and RLRs: a trinity of pathogen sensors that co-operate in innate immunity." Trends Immunol. 27(8):352-7. Epub Jun. 27, 2006.
Dai et al., "Extracellular high mobility group box1 (HMGB1) inhibits enterocyte migration via activation of toll like receptor 4 and increased cell-matrix adhesiveness", *J Biol Chem.*, 2010; 285:4995-5002.
Daubenberger, 2007, "TLR9 agonists as adjuvants for prophylactic and therapeutic vaccines." Curr. Opin. Molec. Ther. 9:45-52.
Ding et al., 1998, "Characterization and quantitation of NF-kappaB nuclear translocation induced by interleukin-1 and tumor necrosis factor-alpha. Development and use of a high capacity fluorescence cytometric system." J Biol Chem. 273(44):28897-905.
Diwan et al., "Enhancement of immune responses by co-delivery of a CpG oligodeoxynucleotide and tetanus toxoid in biodegradable nanospheres", *J. Control Release*, 85(1-3):247-262 (2002).
Duffy et al., "Concordance of bacterial cultures with endotoxin and interleukin-6 in necrotizing enterocolitis", *Dig Dis Sci.* 1997; 42:359-365.
Ewaschuk et al., 2007, "Surface expression of Toll-like receptor 9 is upregulated on intestinal epithelial cells in response to pathogenic bacterial DNA." Infect Immun. 75(5):2572-9. Epub Feb. 26, 2007.
Ey et al., "TLR2 mediates gap junctional intercellular communication through connexin-43 in intestinal epithelial barrier injury", *The Journal of Biological Chemistry*, 284:22332-22343 (2009).
Feng et al., "Heparin-binding epidermal growth factor-like growth factor promotes enterocyte migration and proliferation in neonatal rats with necrotizing enterocolitis", *J Pediatr Surg.*, 2007; 42:214-220.

(56) References Cited

OTHER PUBLICATIONS

Feng et al., 2005, "Heparin-binding EGF-like growth factor (HB-EGF) and necrotizing enterocolitis." Semin Pediatr Surg. 14(3):167-74.
Franchi et al., 2008, "Intracellular NOD-like receptors in innate immunity, infection and disease." Cell Microbiol 10:1-8.
Fukata et al., "Cox-2 is regulated by Toll-like receptor-4 (TLR4) signaling: Role in proliferation and apoptosis in the intestine", *Gastroenterology*, 2006; 131:862-877.
Fukata et al., "Innate immune signaling by Toll-like receptor-4 (TLR4) shapes the inflammatory microenvironment in colitis-associated tumors", *Inflamm Bowel Dis*. 2009; 15:997-1006.
Fukata et al., "TLR4 signaling in the intestine in health and disease", *Biochemical Society Transactions*, 35(6):1473-1478 (2007).
Fukata et al., "Toll-like receptor-4 is required for intestinal response to epithelial injury and limiting bacterial translocation in a murine model of acute colitis", *Am J Physiol Gastrointest Liver Physiol.*, 2005; 288:G1055-G1065.
Gagliardi et al., "Necrotising enterocolitis in very low birth weight infants in Italy: incidence and non-nutritional risk factors", *J. Pediatr Gastroenterol Nutr.*, 2008; 47(2):206-210.
Goodenough, "Bulk isolation of mouse hepatocyte gap junctions. Characterization of the principal protein connexin", *J. Cell Biol.*, 1974; 61: 557-563.
Goodenough, "The structure of cell membranes involved in intercellular communication", *Am. J. Clin. Pathol.*, 1975; 63:636-645.
Grave et al., "New therapies and preventive approaches for necrotizing enterocolitis: report of a research planning workshop", *Pediatr Res.*, 2007; 62:510-514.
Gribar et al., "Reciprocal expression and signaling of TLR4 and TLR9 in the pathogenesis and treatment of necrotizing enterclitis", *Journal of Immunologists*, 182(1):636-646 (2009).
Gribar et al., 2008, "The role of epithelial Toll-like receptor signaling in the pathogenesis of intestinal inflammation." J Leukoc Biol. 83(3):493-8. Epub Dec. 26, 2007.
Grimm et al., "NOD2 Mutations and Crohn's Disease: Are Paneth Cells and Their Antimicrobial Peptides the Link?" Gut; 53(11): 1558-1560, Nov. 2004, entire document especially p. 2.
Guthrie et al., 2003, "Necrotizing enterocolitis among neonates in the United States." J Perinatol 23:278-285.
Halpern et al., "Reduction of experimental necrotizing enterocolitis with anti-TNF-alpha", Am J Physiol Gastrointest Liver Physiol 290:757-764, 2006, First published Nov. 3, 2005, entire document especially abstract; p. 1.
Halpern et al., 2006, "Reduction of experimental necrotizing enterocolitis with anti-TNF-α." Am J. Physiol Gastrointest Liver Physiol 290, pp. G757-G764.
Henry et al., 2005, "Surgical therapy for necrotizing enterocolitis: bringing evidence to the bedside." Semin Pediatr Surg. 14(3):181-90.
Henry et al., 2006, "Laparotomy Versus Peritoneal Drainage for Perforated Necrotizing Enterocolitis." Neoreviews 7:456-462.
Hotta et al., "Lipopolysaccharide-induced colitis in rabbits", *Res Exp Med (Berl)* 1986; 186:61-69.
Hsueh et al., 2003, "Neonatal necrotizing enterocolitis: clinical considerations and pathogenetic concepts." Pediatr Dev Pathol 6:6-23.
Hugot et al., "Association of NOD2 leucine-rich repeat variants with susceptibility to Crohn's disease." Nature. 411(6837):599-603 (2001).
International Search Report for PCT/US2011/053293, dated Apr. 9, 2012.
InvivoGen: Delivering Genes. "TLR9 Ligands." Downloaded on Apr. 16, 2007 from hrrp://www.invivogen.com/family.php?ID=104&ID_cat=2&ID_sscat=9.
Iwasaki et al., "Regulation of adaptive immunity by the innate immune system", *Science*, 2010; 327:291-295.
Izumi et al., "Platelet-activating factor receptor: gene expression and signal transduction", *Biochim Biophys Acta*, 1995; 1259:317-333.

Jesse et al., 2006, "Necotrizing enterocolitis: Relationship to Innate Immunity, Clinical Features, and Strategies for Prevention." NeoReviews 7:143-150.
Jilling et al., "The roles of bacteria and TLR4 in rat and murine models of necrotizing enterocolitis." J Immunol. 177(5):3273-82 (2006).
Kanneganti et al., 2007, "Intracellular NOD-like receptors in host defense and disease." Immunity 27:549-559.
Katakura et al., "Toll-like receptor 9-induced type I IFN protects mice from experimental colitis." J Clin Invest. 115(3):695-702. Erratum in: J Clin Invest. 2005 115(4):1100 (2005).
Kitagaki et al., "Oral administration of CpG-ODNs suppresses antigen-induced asthma in mice", *British Society for Immunology, Clinical and Experimental Immunology*, 143:249-259 (2005).
Knapp, et al., "Thionation: GlcNAc-Thiazoline Triacetate {(3aR,5R,6S,7R,7aR)-5-Acetoxymethyl-6, 7-Diacetoxy-2-Methyl-5,6,7,7a-Tetrahydro-3aH-Pyrano[3,2-d]Thiazole}", Organic Syntheses, 84:68-76 (2007).
Kobayashi et al., "Suppression of murine endotoxin response by E5531, a novel synthetic lipid A antagonist." Antimicrob Agents Chemother. 42(11):2824-9 (1998).
Kosloske, 1994, "Epidemiology of necrotizing enterocolitis." Acta Pediatr. Suppl. 396:2-7.
Krieg, 2006, "Therapeutic potential of Toll-like receptor 9 activation." Nat. Rev. Drug Disc. 5:471-484.
Kruis et al., "Circulating lipid A antibodies despite absence of systemic endotoxemia in patients with Crohn's disease", *Dig Dis Sci.*, 1984; 29:502-507.
Laird, "Connexin phosphorylation as a regulatory event linked to gap junction internalization and degradation", *Biochi. Biophys. Acta*, 2005; 1711: 172-182.
Lampe et al., "Phosphorylation of connexin-43 on serine 368 by protein kinase C regulates gap junction communication", *J. Cell Biol.*, (2000) 149:1503-1512.
Leapart et al., "Interferon-γ inhibits enterocyte migration by reversibly displacing connexion43 from lipid rafts", *Am J Physiol Gastrointest Liver Physiol*, 2008; 295:G559-G569.
Leaphart et al., 2007, "Interferon-gamma inhibits intestinal restitution by preventing gap junction communication between enterocytes." Gastroenterology. 132(7):2395-411. Epub Mar. 21, 2007.
Leaphart et al., 2007. "A Critical Role for TLR4 in the Pathogenesis of Necrotizing Enterocolitis by Modulating Intestinal Injury and Repair." J Immunology 179:4808-4820.
Lee et al., 2006, "Homeostatic effects of TLR9 signaling in experimental colitis." Ann NY Acad Sci. 1072:351-5.
Lemaitre et al., "The dorsoventral regulatory gene cassette spätzle/Toll/cactus controls the potent antifungal response in *Drosophila* adults", *Cell*, 1996; 86:973-983.
Lin et al., "Oral probiotics reduce the incidence and severity of necrotizing enterocolitis in very low birth weight infants", *Pediatrics*, 2005; 115:1-4.
Lin et al., 2006, "Necrotising enterocolitis." Lancet 368:1271-1283.
Liu et al., "Changes in intestinal toll-like receptors and cytokines precede histological injury in a rat model of necrotizing enterocolitis", *Am J Physiol Gastrointest Liver Physiol.*, 2009; 297:G442-G450.
Lotz et al., "Postnatal acquisition of endotoxin tolerance in intestinal epithelial cells", *J Exp Med.*, 2006; 203:973-984.
Lu et al., "Polyunsaturated fatty acid supplementation alters proinflammatory gene expression and reduces the incidence of necrotizing enterocolitis in a neonatal rat model", *Pediatr Res.*, 2007; 61:427-432.
Luig et al., "Epidemiology of necrotizing enterocolitis—PartI: Changing regional trends in extremely preterm infants over 14 years", *J. Paediatr Child Health*, 2005; 41(4):169-73.
Macagno et al., 2006, "A cyanobacterial LPS antagonist prevents endotoxin shock and blocks sustained TLR4 stimulation required for cytokine expression." J. Exp. Med. 203(6):1481-1492.
Maeda et al., 2005, "Nod2 mutation in Crohn's disease potentiates NF-kappaB activity and IL-1beta processing." Science 307:734-738. Erratum in Science. Apr. 29, 2005;308(5722):633.

(56) References Cited

OTHER PUBLICATIONS

Medzhitov et al., "A human homologue of the *Drosophila* Toll protein signals activation of adaptive immunity", *Nature*, 1997; 388:394-397.
Merck Manual website, Nov. 2007 by William J. Cochran, MD. Downloaded on Nov. 7, 2011 from <http://www.merckmanuals.com/professional/pediatrics/gastrointestinal_disorders_in_neonates_and_infants/necrotizing_enterocolitis.html>.
Michaelsson et al., "Regulation of T cell responses in the developing human fetus", *J. Immunol.*, 2006; 176(10):5741-5748.
Milla et al., "Small intestinal motility patterns in the perinatal period", *J Pediatr. Gastroenterol Nutr.*, 1983; 2:S141-S144.
Mizrahi et al., "Necrotizing enterocolitis in premature infants", *J Pediatr.*, 1965; 66:697-705.
Moss et al., 2006, "Laparotomy versus peritoneal drainage for necrotizing enterocolitis and perforation." N. Engl. J. Med. 354:2225-2234.
Muguruma et al., "The central role of PAF in necrotizing enterocolitis development", *Adv Exp Med Biol*. 1997; 407:379-382.
Mullarkey et al., 2003, "Inhibition of endotoxin response by e5564, a novel Toll-like receptor 4-directed endotoxin antagonist." J Pharmacol Exp Ther. 304(3):1093-102.
Neal et al., "A critical role for TLR4 induction of autophagy in the regulation of enterocyte migration and the pathogenesis of necrotizing enterocolitis", *J. Immunol.*, 2013; 190(7):3541-3551.
Neal et al., "Enterocyte TLR4 mediates phagocytosis and translocation of bacteria across the intestinal barrier." J Immunol. 176(5):3070-9 (2006).
Neu et al., 2005, "Intestinal innate immunity: how does it relate to the pathogenesis of necrotizing enterocolitis." Semin. Pediatr. Surg. 14: 137-144.
Neu, 1996, "Necrotizing enterocolitis: the search for a unifying pathogenic theory leading to prevention." Pediatr Clin North Am. 43(2):409-32.
Ng, 2001, "Necrotizing enterocolitis in the full-term neonate." J Paediatr Child Health. 37(1):1-4.
Noerr, "Current controversies in the understanding of necrotizing enterocolitis", *Adv Neonatal Care*, 2003; 3:107-120.
Obermeier et al. 2002, "CpG motifs of bacterial DNA exacerbate colitis of dextran sulfate sodium-treated mice." Eur J Immunol. Jul. 2002;32(7):2084-92.
Obermeier et al., "Contrasting activity of cytosin-guanosin dinucleotide oligonucleotides in mice with experimental colitis", *Clin Exp Immunol.*, 134(2):217-224 (2003).
Ogura et al., "A frameshift mutation in NOD2 associated with susceptibility to Crohn's disease." Nature. 411(6837):603-6 (2001).
Otte et al., 2004, "Mechanisms of cross hyporesponsiveness to Toll-like receptor bacterial ligands in intestinal epithelial cells." Gastroenterology. 126(4):1054-70.
Panigrahi, "Necrotizing enterocolitis", *Paediatr. Drugs*, 2006; 8(3):151-165.
Pierro, 2005, "The surgical management of necrotising enterocolitis." Early Hum Dev. 81(1):79-85.
Poltorak et al., 1998, "Defective LPS Signaling in C3H/HeJ and C57BL/10ScCr Mice: Mutations in Tlr4 Gene." Science 282: 2085-2088.
Prohinar et al., "Specific high affinity interactions of monomeric endotoxin.protein complexes with Toll-like receptor 4 ectodomain." J Biol Chem. 282(2):1010-7. (2007).
Putta et al., 2006, "Novel oligodeoxynucleotide agonists of TLR9 containing N3-Me-dC or N1-Me-dG modifications." Nucleic Acids Res. 34(11):3231-8.
Qureshi et al., "Increased expression and function of integrins in enterocytes by endotoxin impairs epithelial restitution", *Gastroenterology*, 2005; 128:1012-1022.
Rachmelewitz et al., 2004, "Toll-like receptor 9 signaling mediates the anti-inflammatory effects of probiotics in murine experimental colitis." Gastroenterology. 126(2):520-8.
Rakoff-Nahoum et al., "Recognition of commensal microflora by toll-like receptors is required for intestinal homeostasis", *Cell*, 2004; 118:229-241.
Richardson, et al., "Nucleotide-binding Oligomerization Domain-2 Inhibits Toll Like Receptor-4 Signaling in the Intestinal Epithelium", Gastroenterology, 139(3):904-917 (2010).
Roach et al., "The evolution of vertebrate Toll-like receptors", *PNAS*, 2005; 102:9577-9582.
Rossignol et al., 2004, "Safety, pharmacokinetics, pharmacodynamics, and plasma lipoprotein distribution of eritoran (E5564) during continuous intravenous infusion into healthy volunteers." Antimicrob Agents Chemother. 48(9):3233-40.
Shan et al., "Regulation of toll-like receptor 4-induced proasthmatic changes in airway smooth muscle function by opposing actions of ERK1/2 and p38 MAPK signaling", *Am J. Physiol. Lung Cell Mol. Physiol.*, 291(3):L324-L333 (2006).
Sharma et al., 2007, "Neonatal gut barrier and multiple organ failure: role of endotoxin and proinflammatory cytokines in sepsis and necrotizing enterocolitis." J Pediatr Surg 42:454-461.
Shin et al., 2000, "Diminished epidermal growth factor levels in infants with necrotizing enterocolitis." J Pediatr Surg. 35(2):173-6; discussion 177.
Shindou et al., "Roles of cytosolic phospholipase A2 and platelet-activating factor receptor in the Ca-induced biosynthesis of PAF", *Biochem Biophys Res Commun.* 2000; 271:812-817.
Shuto et al., "Activation of NF-kappa B by nontypeable hemophilus influenzae is mediated by toll-like receptor 2-TAK1-dependent NIK-IKK alpha/beta-I kappa B alpha and MKK3/6-p38 MAP kinase signaling pathways in epithelial cells", *PNAS*, 98(15):8774-8779 (2001).
Sodhi, et al., "DNA Attenuates Enterocyte Toll-like Receptor 4-Mediated Intestinal Mucosal Injury After Remote Trauma", Am J Physiol Gastrointest Liver Physiol., 300:G862-G873 (2011).
Sodhi, et al., "Toll-like-receptor-4 Inhibits Enterocyte Proliferation via Impaired β-Catenin Signaling in Necrotizing Enterocolitis", Gastroenterology, 138(1):185 (2010).
Strober et al., 2006, "Signalling pathways and molecular interactions of NOD1 and NOD2." Nat Rev Immunol. 6:9-20.
Supplemental European Search Report for EP Application No. 08746070.5, dated May 25, 2011.
Svetlov et al., "Regulation of platelet-activating factor (PAF) biosynthesis via coenzyme A-independent transacylase in the macrophage cell line IC-21 stimulated with lipopolysaccharide", *Biochim Biophys Acta*, 1997; 1346:120-130.
Takeda et al., "Toll-like receptors in innate immunity." Int Immunol. 17(1):1-14.
Takeda et al., 2001, "Roles of Toll-like receptors in innate immune responses." Genes Cells 6:733-742.
Tatum et al., "The role of toll-like receptor 9 in an animal model of necrotizing enterocolitis", *Journal of Investigative Medicine*, 58(2):436 (2010).
Thompson et al., "Necrotizing enterocolitis in newborns", *Drugs*, 2008; 68(9):1227-1238.
Uauy et al., 1991, "Necrotizing enterocolitis in very low birth weight infants: biodemographic and clinical correlates." National Institute of Child Health and Human Development Neonatal Research Network. J Pediatr 119:630-638.
University of Pittsburgh Department of Critical Care Medicine: Research—The Crisma Laboratory, pp. 1-11. Downloaded on Apr. 19, 2007 from http:/www.ccm.upmc.edu/research/res_crisma.htlm.
Van Heel et al., "Synergy between TLR9 and NOD2 innate immune responses is lost in genetic Chrohn's disease" *GUT, British Medical Association*, 54(11):1553-1557 (2005).
Verma et al., "Novel pharmacophores of connexin-43 based on the "RXP" series of Cx43-binding peptides", *Circ. Res.*, 2009; 105(2):176-184.
Verthelyi et al., "Human peripheral blood cells differentially recognize and respond to two distinct CPG motifs." J Immunol. 166(4):2372-7 (2001).
Vink et al., 2002, "In vivo evidence for a role of toll-like receptor 4 in the development of intimal lesions." Circulation. 106(15):1985-90.

(56) References Cited

OTHER PUBLICATIONS

Wang et al., "NF-κB-mediated expression of MAPK phosphatase-1 is an early step in desensitization to TLR ligands in enterocytes", *Mucosal Immunol.*, 2010; 3:523-534.

Wang et al., "Ubiquitin-editing enzyme A20 promotes tolerance to lipopolysaccharide in enterocytes", *J Immunol.*, 2009; 183:1384-1392.

Warner et al., 2005, "Role of epidermal growth factor in the pathogenesis of neonatal necrotizing enterocolitis." Semin Pediatr Surg. 14(3):175-80.

Watanabe et al., "Muramyl dipeptide activation of nucleotide-binding oligomerization domain 2 protects mice from experimental colitis." J Clin Invest 118:545-559 (2008).

Wirtz et al., "Illuminating the role of type I IFNs in colitis." J Clin Invest. 115(3):586-8 (2005).

Wolfs et al., "Localization of the lipopolysaccharide recognition complex in the human healthy and inflamed premature and adult gut", *Inflamm Bowel Dis.*, 2010; 16:68-75.

Worthen et al., "The priming of neutrophils by lipopolysaccharide for production of intracellular platelet-activating factor: potential role in mediation of enhanced superoxide secretion", *J Immunol.*, 1988; 140:3553-3559.

Wynn et al., "The host response to sepsis and developmental impact", *Pediatrics*, 2010; 125:1031-1041.

Yang et al., "NOD2 transgenic mice exhibit enhanced MDP-mediated down-regulation of TLR2 responses and resistance to colitis induction." Gastroenterology 133:1510-1521 (2007).

Yang et al., 2005, "Role of Toll-like receptor 4/NF-kappaB pathway in monocyte-endothelial adhesion induced by low shear stress and ox-LDL." Biorheology. 42(3):225-36.

Yang et al., 2007, "NOD2 pathway activation by MDP or Mycobacterium tuberculosis infection involves the stable polyubiquitination of Rip2." J Biol Chem 282:36223-36229.

Zhai et al., "Cutting edge: TLR4 activation mediates liver ischemia/reperfusion inflammatory response via IFN regulatory factor 3-dependent MyD88-independent pathway", *J. Immunol.*, 173(12):7115-7119 (2004).

Zheng et al., "Regulation of colonic epithelial repair in mice by Toll-like receptors and hyaluronic acid", *Gastroenterology*, 2009; 137:2041-2051.

Zhou et al., "Oral administration of plant-based rotavirus VP6 induces antigen-specific IgAs, IgGs and passive protection in mice" *Vaccine*, 28:6021-6027 (2010).

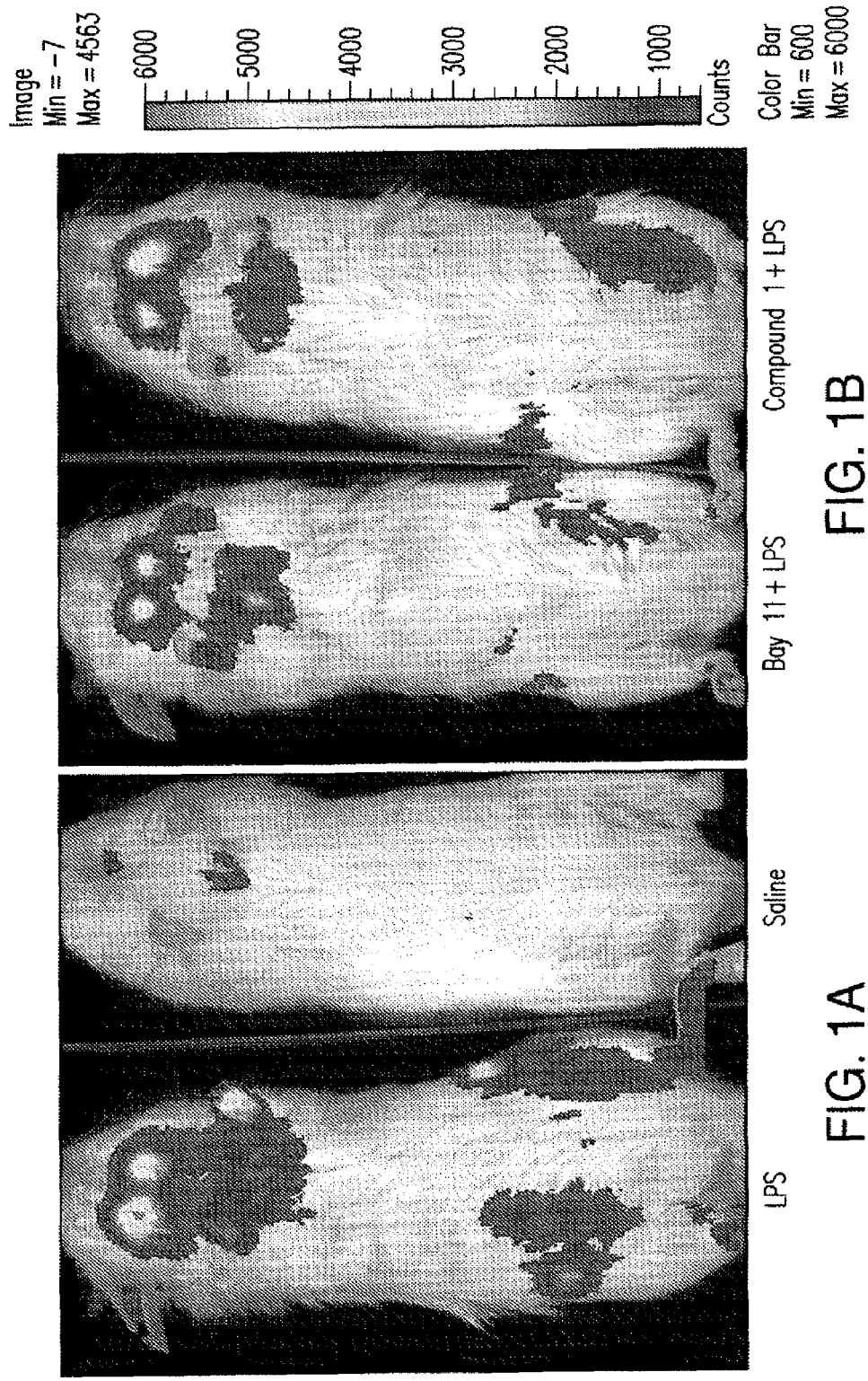

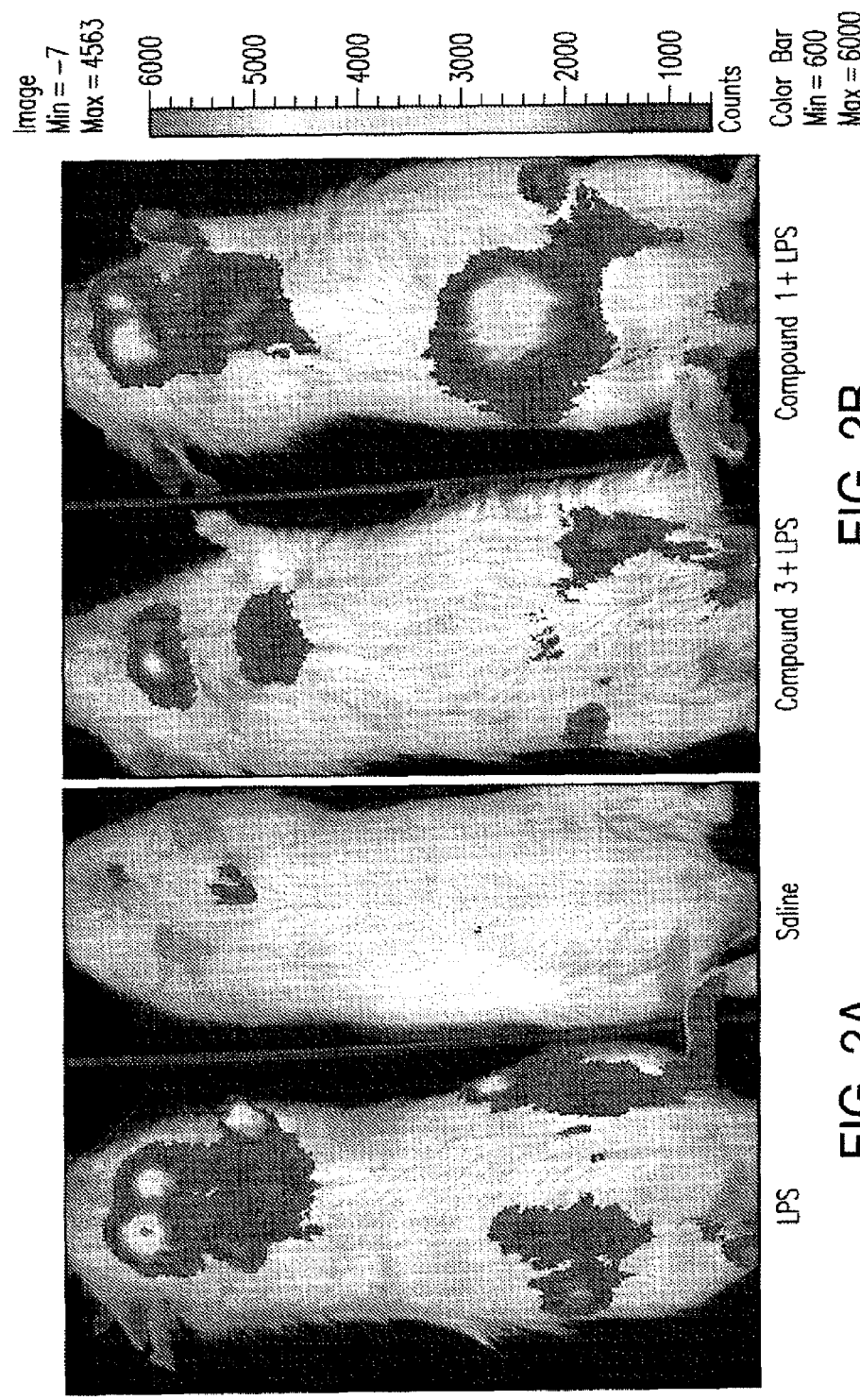

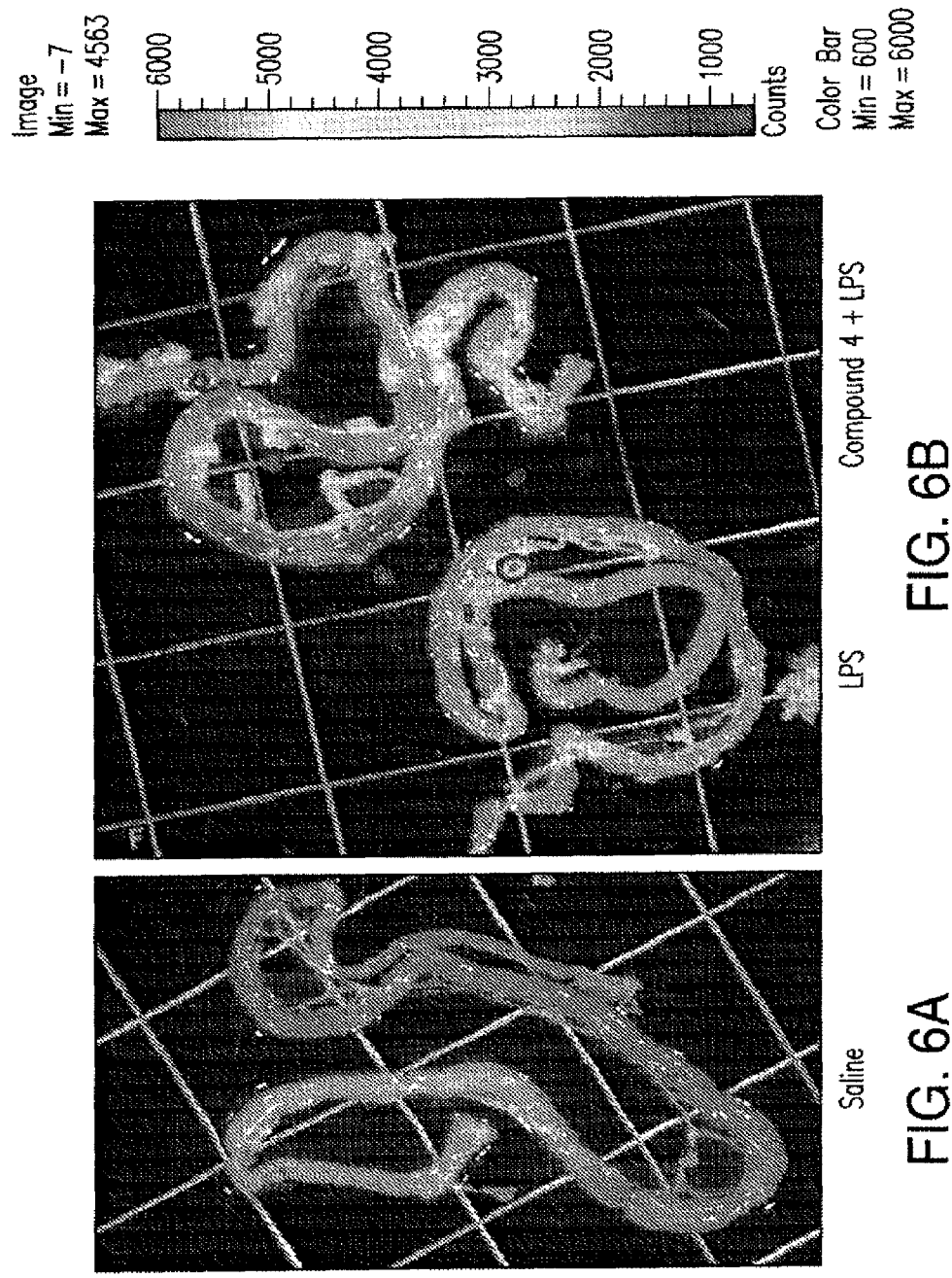

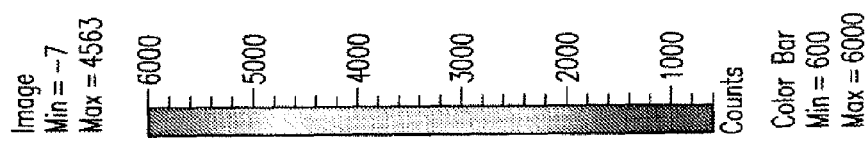
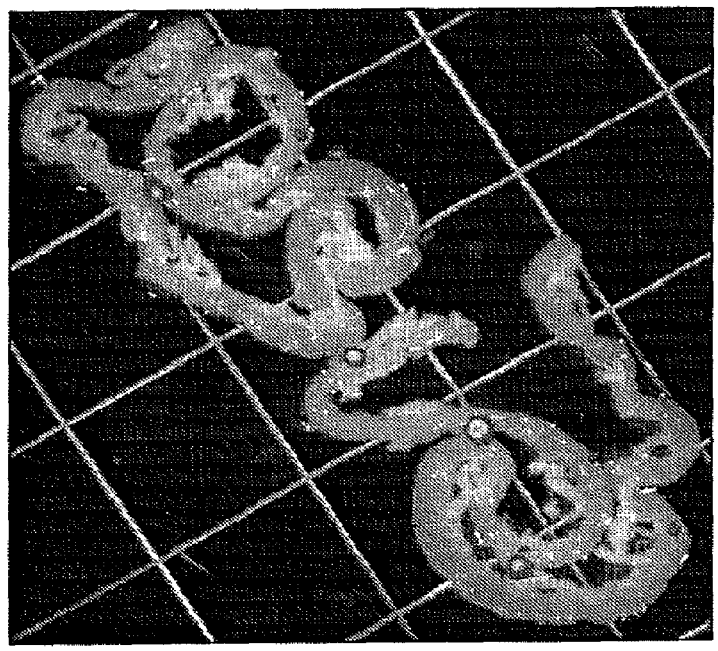
FIG. 7B
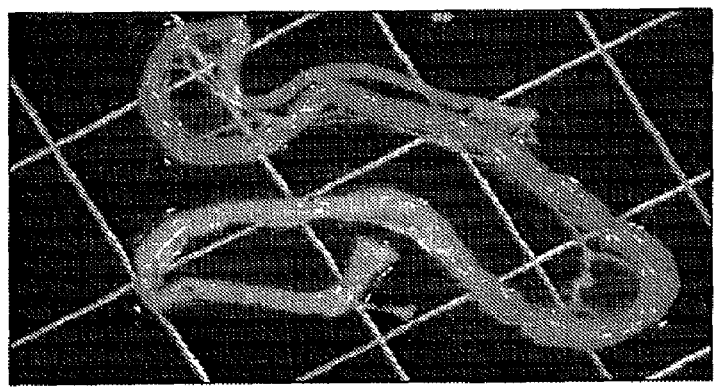
FIG. 7A

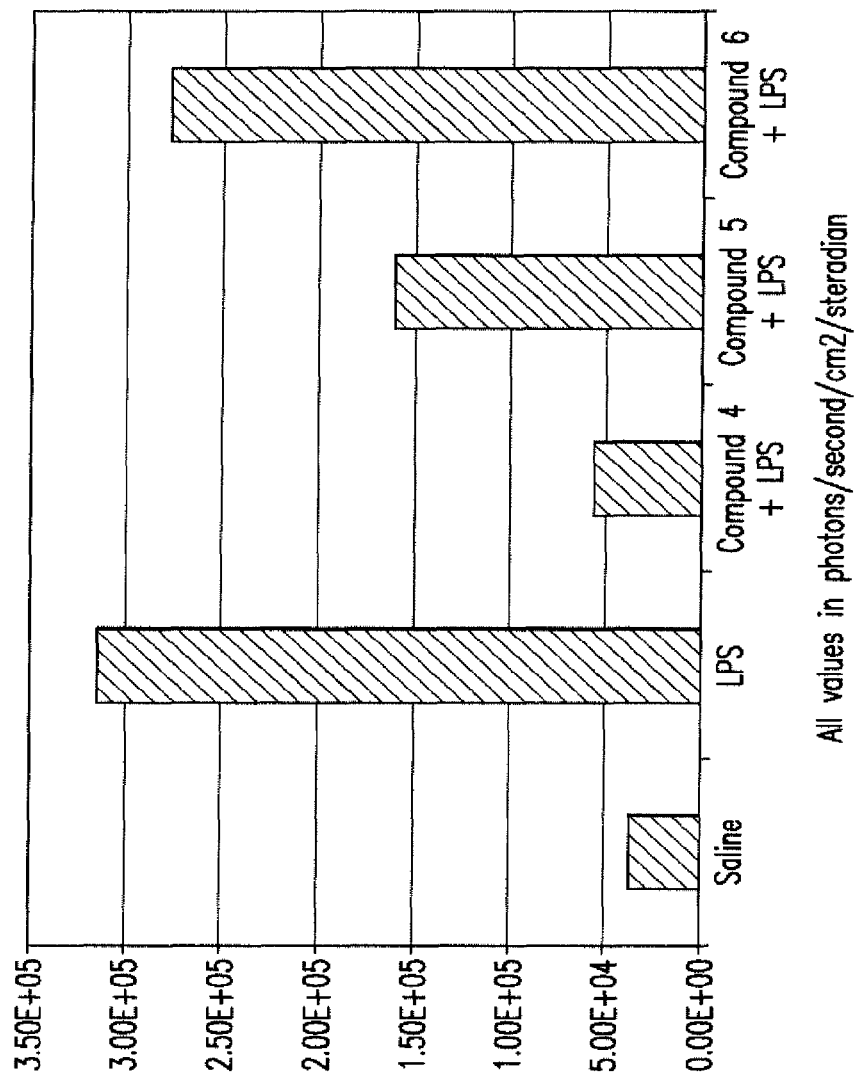

| Compound | Tested by NFkB luciferase? | Tested by CFW endotoxemia? | endotox* | ELISA IL-6 |
|---|---|---|---|---|
| Saline | Y | Y | 0 | 0 |
| LPS | Y | Y | 2 | 1.511 |
| Bay 11 + LPS | Y | Y | 1 | 0.44 |
| 1 | Y | Y | 3 | 0.846 |
| 2 | Y | Y | 2 | 1.177 |
| 3 | Y | Y | 1 | 1.31 |
| 4 | Y | Y | 0 | 0.461 |
| 5 | Y | Y | 3 | above scale |
| 6 | Y | Y | 2 | 1.635 |
| 7 | | Y | 2 | 0.364 |
| 8 | | Y | 0 | 0.115 |
| 9 | | Y | 2 | 0.985 |
| 10 | | Y | 2 | 1.315 |
| 11 | | Y | 2 | 1.617 |
| 12 | | Y | 2 | 1.176 |
| 13 | | Y | 2 | 0.614 |
| 14 | | Y | 3 | 0.826 |
| 15 | | Y | 2 | 1.445 |
| 16 | | Y | 1 | 1.051 |
| 17 | | Y | 2 | 0.193 |
| 18 | | Y | 2 | 1.708 |
| 19 | | Y | 2 | 1.071 |
| 20 | | Y | 2 | 0.624 |
| 21 | | Y | 1 | 0.375 |
| 22 | | Y | 1 | 0.571 |
| 23 | | Y | 2 | 0.257 |
| 24 | | Y | 2 | 0.611 |
| 25 | | Y | 3 | 0.606 |
| 26 | | Y | 2 | 0.279 |
| 27 | | Y | 0 | 0.324 |
| 28 | | Y | 3 | 0.277 |
| 29 | | Y | 2 | 0.203 |
| 30 | | Y | 2 | 0.231 |
| 31 | | Y | 3 | 0.469 |
| 32 | | Y | 3 | 0.809 |
| 33 | | Y | 2 | 0.9 |
| 34 | | Y | 0 | 0.881 |
| 35 | | Y | 1 | 0.574 |
| 36 | | Y | 1 | 0.451 |
| 37 | | Y | 3 | 1.252 |
| 38 | | Y | 3 | 1.593 |
| 39 | | Y | 2 | 0.957 |

FIG. 9A

| | | | |
|---|---|---|---|
| 40 | Y | 3 | 1.691 |
| 41 | Y | 3 | 1.378 |
| 42 | Y | 1 | 0.718 |
| 43 | Y | 1 | 0.201 |
| 44 | Y | 2 | 0.254 |
| 45 | Y | 2 | 0.276 |
| 46 | Y | 2 | 0.468 |
| 47 | Y | 1 | 0.134 |
| 48 | Y | 2 | 1.537 |
| 49 | Y | 2 | 2.056 |
| 50 | Y | 1 | 1.571 |
| 51 | Y | 2 | 1.252 |
| 52 | Y | 1 | 1.193 |
| 53 | Y | 2 | 0.853 |
| 54 | Y | 1 | 0.546 |
| 55 | Y | 1 | 0.642 |
| 56 | Y | 1 | 0.813 |
| 57 | Y | 1 | 0.685 |
| 58 | Y | 1 | 0.388 |
| 59 | Y | 1 | 0.164 |
| 60 | Y | 2 | 0.397 |
| 61 | Y | 1 | 0.392 |
| 62 | Y | 4 | 1.798 |
| 63 | Y | 1 | 0.4 |
| 64 | Y | 2 | 0.434 |
| 65 | Y | 2 | 1.12 |

FIG. 9B

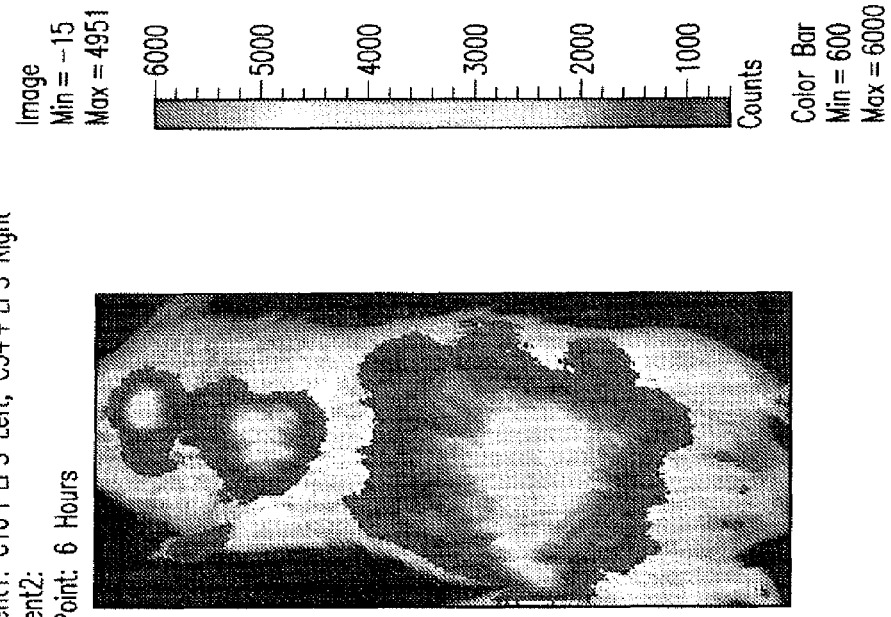
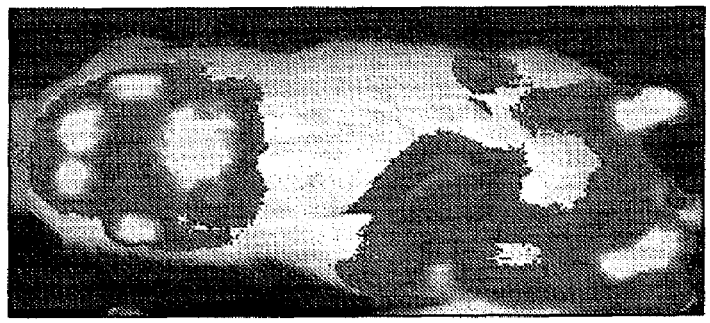
FIG. 10B

TLR4 INHIBITORS FOR THE TREATMENT OF HUMAN INFECTIOUS AND INFLAMMATORY DISORDERS

PRIORITY CLAIM

This application is a continuation of U.S. patent application Ser. No. 13/848,809 filed Mar. 22, 2013, which is a continuation of International Patent Application Serial No. PCT/US2011/053293, filed Monday Sep. 26, 2011, and claims priority to U.S. Provisional Application Ser. No. 61/386,345, filed Sep. 24, 2010 and to U.S. Provisional Application Ser. No. 61/387,335, filed Sep. 28, 2010, the contents of all four of which are hereby incorporated by reference herein in their entireties.

GRANT INFORMATION

Federal funding was not used in the development of the subject matter of the invention.

1. INTRODUCTION

The present invention relates to methods of treating infectious, inflammatory and post-traumatic disorders by administering various compounds newly discovered to have TLR4 inhibitory activity.

2. BACKGROUND OF THE INVENTION

The innate immune receptor Toll-like receptor 4 ("TLR4") has been recognized to be the receptor on hematopoietic and non-hematopoietic cells for endotoxin (lipopolysaccharide, "LPS") as well as a variety of endogenous molecules that are released within the body during inflammatory or infectious disorders. Strategies to discover molecules that are capable of neutralizing the ability of TLR4 to signal are likely to show promise as novel anti-infective and/or antiinflammatory agents.

3. SUMMARY OF THE INVENTION

The present invention relates to methods of treating infectious, inflammatory and post-traumatic disorders by administering various compounds newly discovered to have TLR4 inhibitory activity. Compounds that may be used according to the invention are set forth in TABLE 1, below. In addition to methods of treatment, the present invention further provides for pharmaceutical compositions comprising said compounds, together with a suitable pharmaceutical carrier. Because TLR4 is the most upstream receptor in the pro-inflammatory LPS signaling cascade, treatments of the invention, which inhibit or antagonize TLR4 action, may avoid the pitfalls associated with other cytokine inhibitors that act further down the pathway and accordingly play a less specific (and perhaps non-critical) role.

4. BRIEF DESCRIPTION OF THE FIGURES

FIG. 1A-B. NFkB luciferase reporter mice treated with either (A) LPS (positive control, left) or saline (negative control; right) or (B) Bay-11-7082+LPS (left) or compound 1+LPS (right), imaged using the IVIS Lumina 3D Optical system.

FIG. 2A-B. NFkB luciferase reporter mice treated with either (A) LPS (positive control, left) or saline (negative control, right) or (B) compound 3+LPS (left) or compound 2+LPS (right), imaged using the IVIS Lumina 3D Optical system.

Figure 3B:
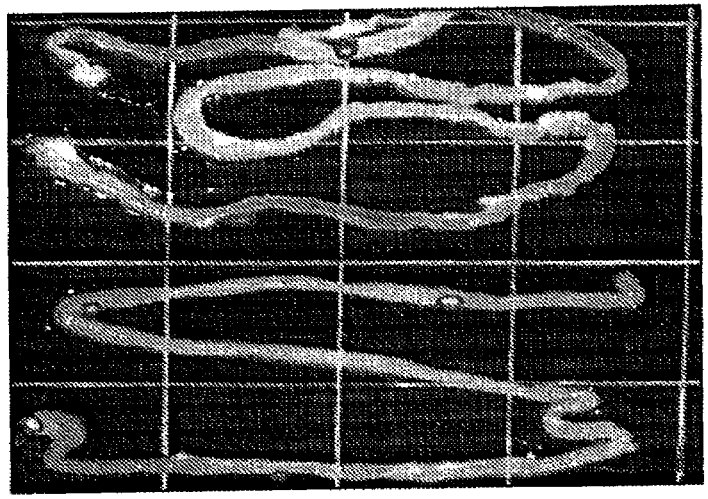
Figure 3C:
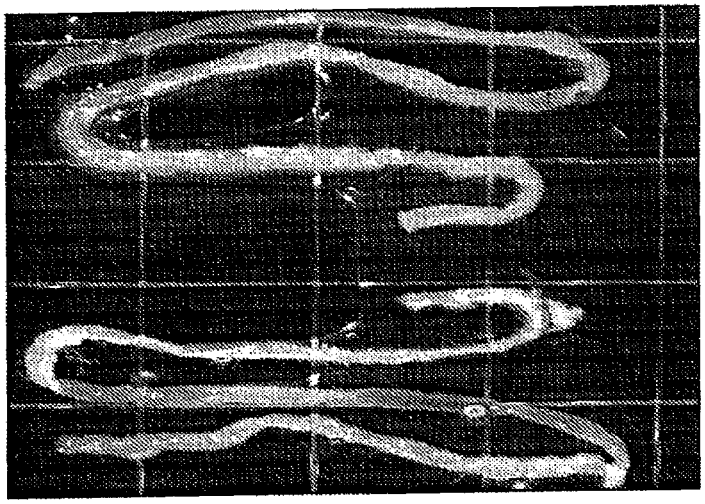

FIG. 3A-C. Intestines from NFkB luciferase reporter mice of FIGS. 1A-B and 2A-B, in particular (A) mice treated with LPS (left) or saline (right) or (B) Bay-11-7082+LPS (left) or compound 1+LPS (right) or (C) compound 2+LPS or compound 3+LPS (left), imaged using the IVIS Lumina 3D Optical system.

Figures 4A, 4B:
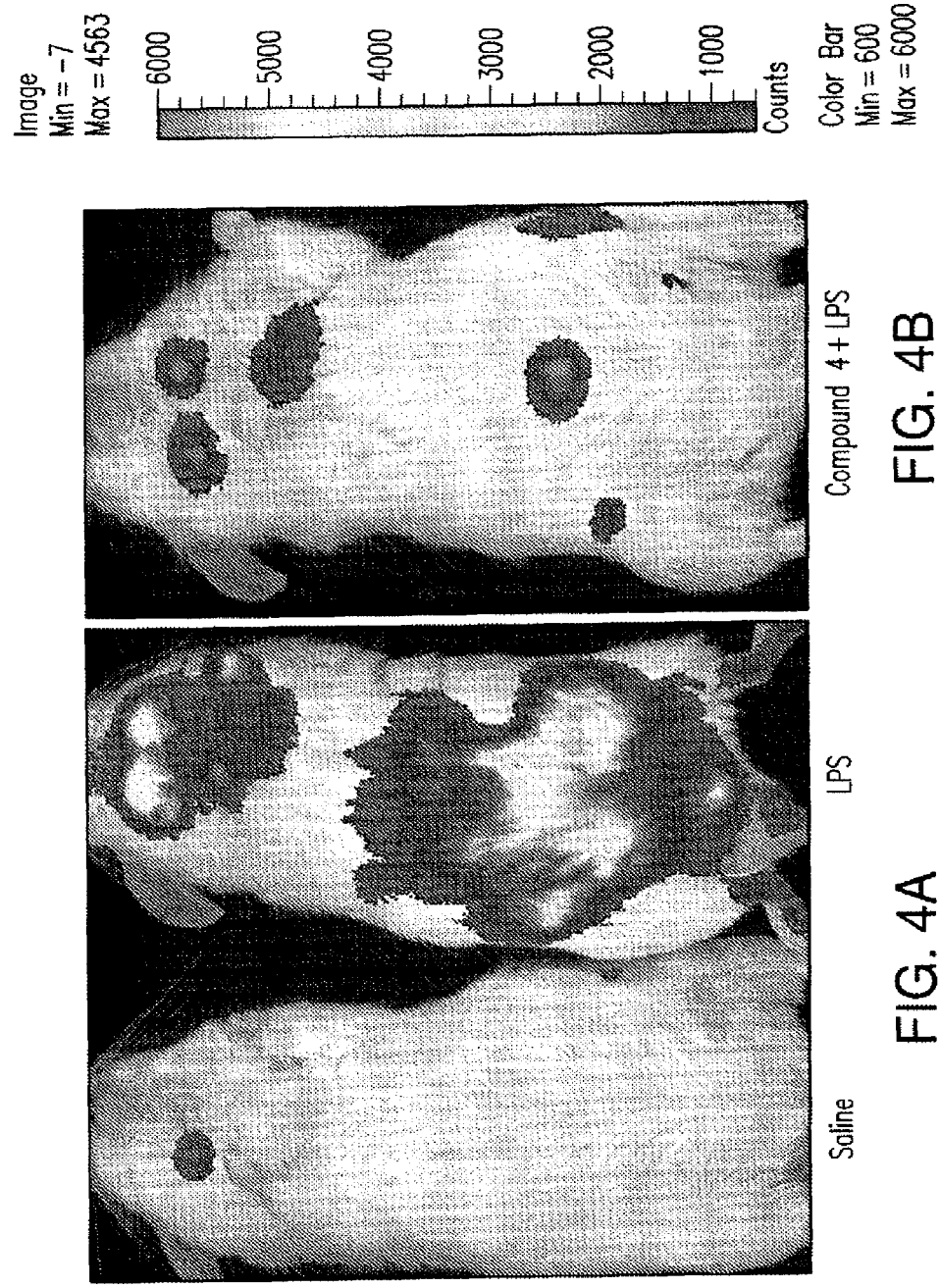

FIG. 4A-B. NFkB luciferase reporter mice treated with either (A) saline (left) or LPS (right) or (B) compound 4+LPS, imaged using the IVIS Lumina 3D Optical system.

Figure 5:
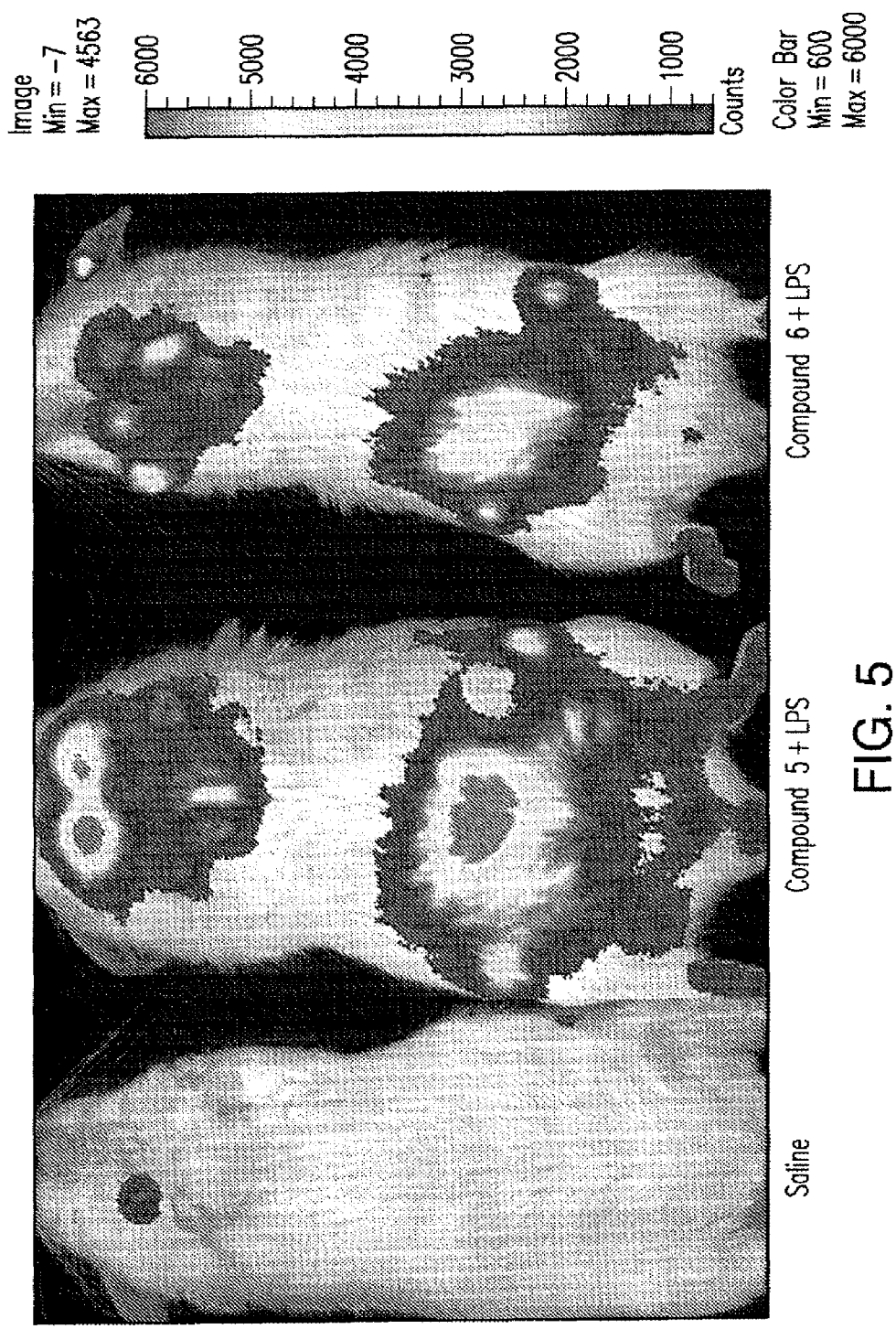

FIG. 5. NFkB luciferase reporter mice treated with either saline (left), compound 5+LPS (center) or compound 6+LPS (right) imaged using the IVIS Lumina 3D Optical system.

FIG. 6A-B. Intestines from NFkB luciferase reporter mice of FIG. 4A-B, in particular mice treated with (A) saline or (B) LPS (left) or compound 4+LPS (right), imaged using the IVIS Lumina 3D Optical system.

FIG. 7A-B. Intestines from NFkB luciferase reporter mice of FIG. 5, in particular mice treated with (A) saline or (B) compound 5+LPS (left) or compound 6+LPS (right), imaged using the IVIS Lumina 3D Optical system.

Figure 8A:
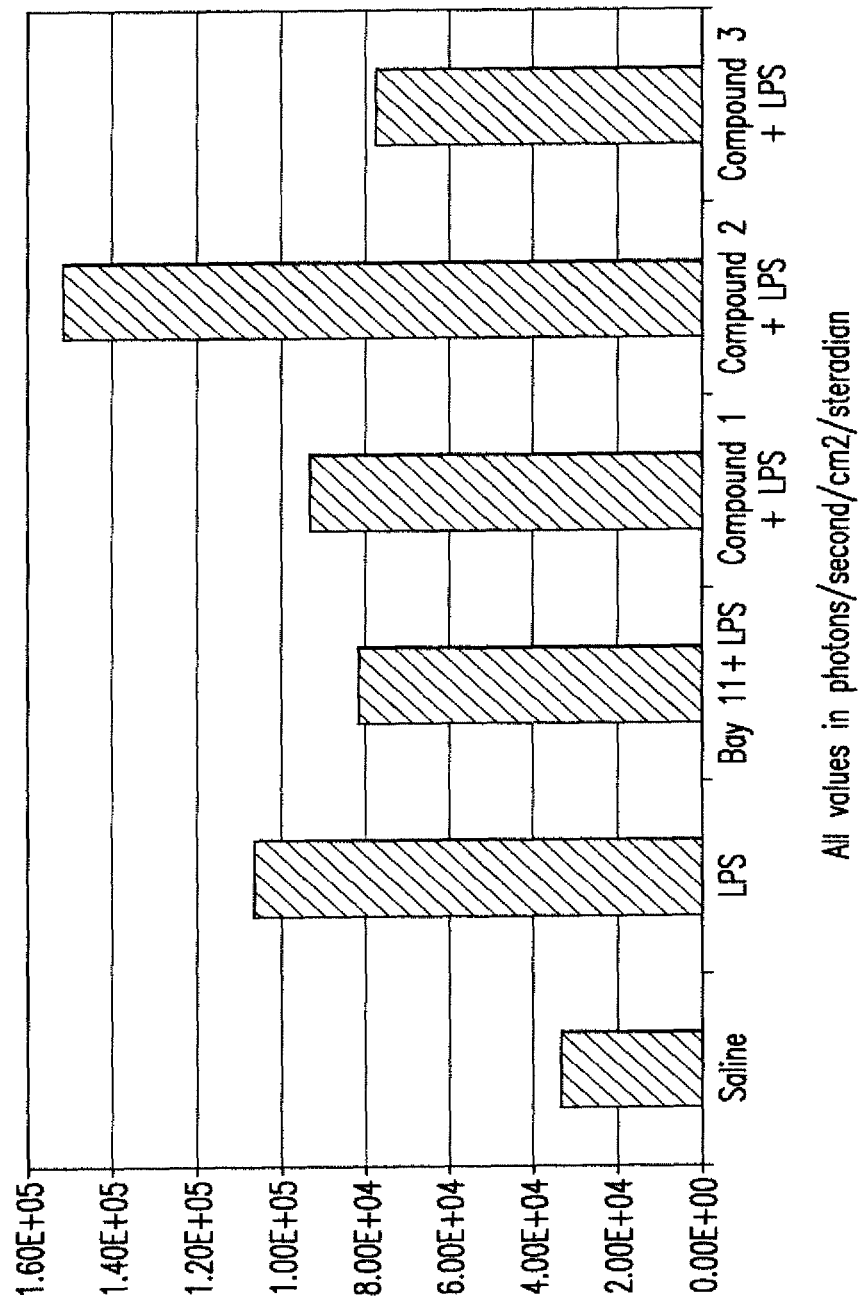

FIG. 8A-B. Summary of results of FIGS. 1-7, above.

FIG. 9A-B. ELISA results showing IL6 production. (*) denotes the endotoxicity score, where 0=healthy, 1=mild, 2=moderate, 3=severe, and 4-lethal. Highlighting denotes particular "hits" of interest.

Figure 10A:
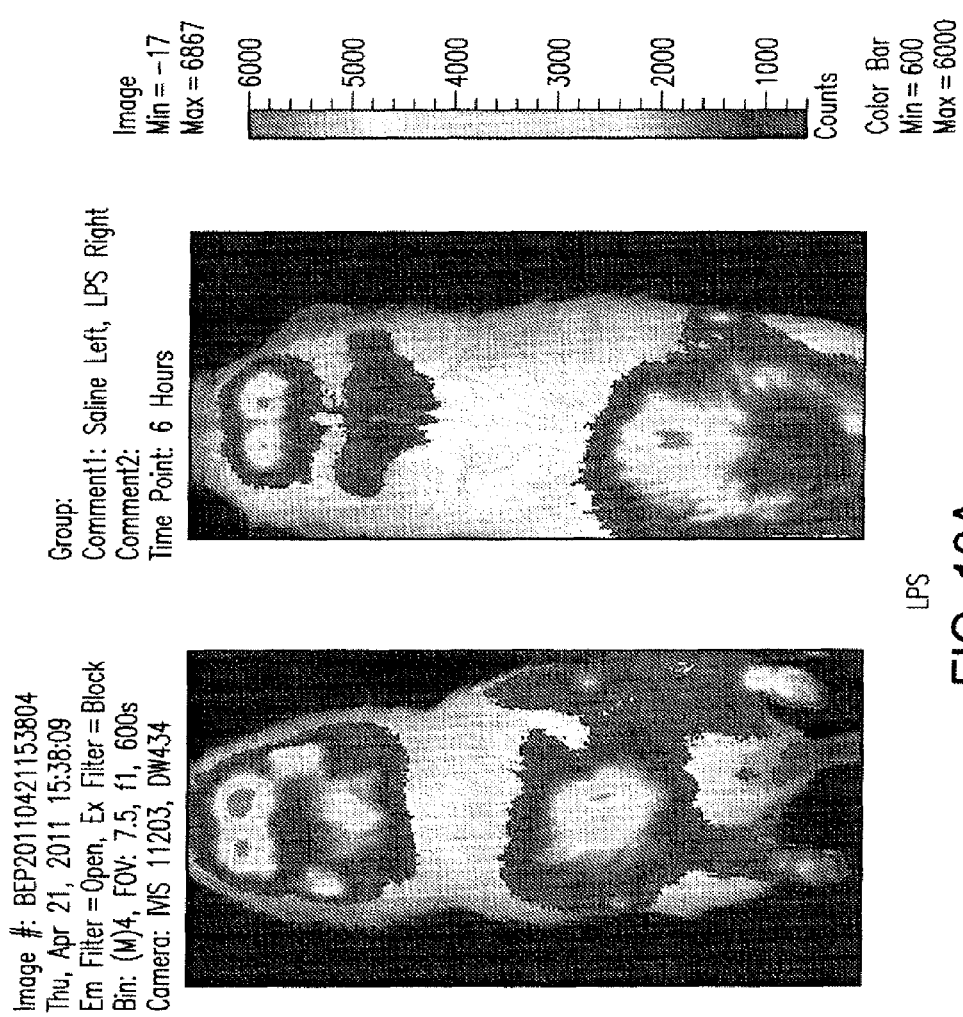

FIG. 10A-B. NFKB luciferase reporter mice treated with either (A) LPS (in the animal on the right with an animal treated with saline control on the left) or (B) LPS plus compound (with the animal on the right treated with C34+LPS and the animal on the left treated with C16+LPS).

Figure 11:
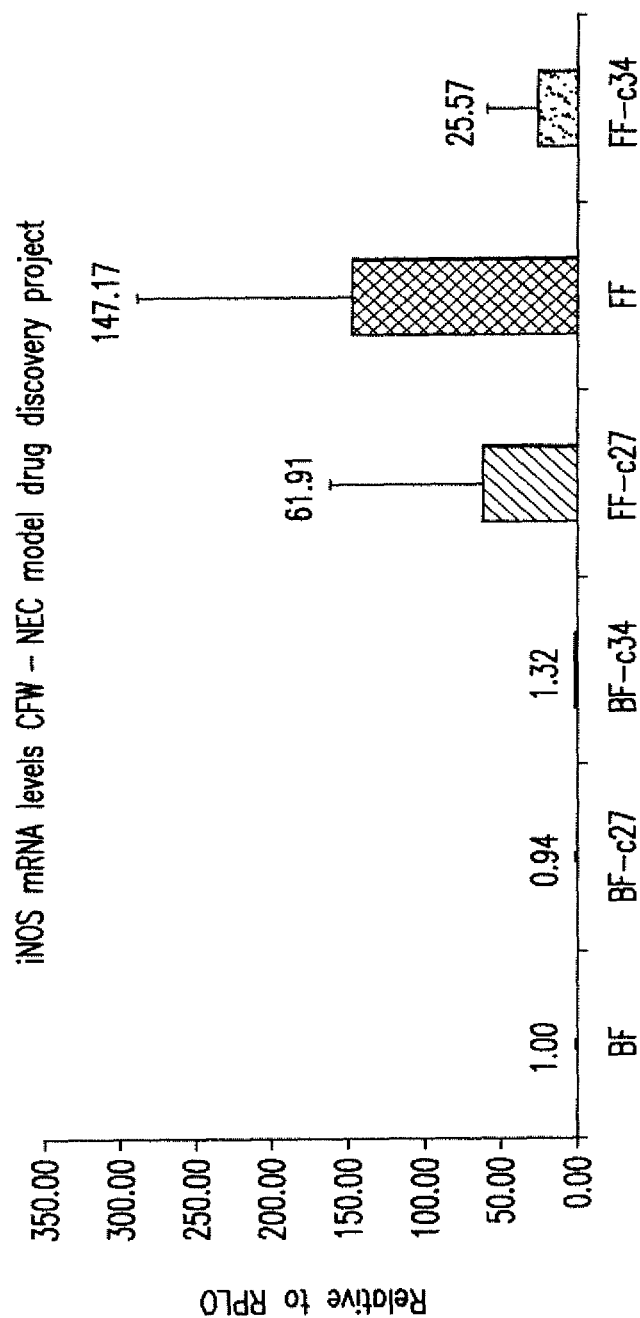

FIG. 11. iNOS mRNA levels in breast-fed (BF) controls and a CFW-NEC model induced by formula feeding (FF).

Figure 12:
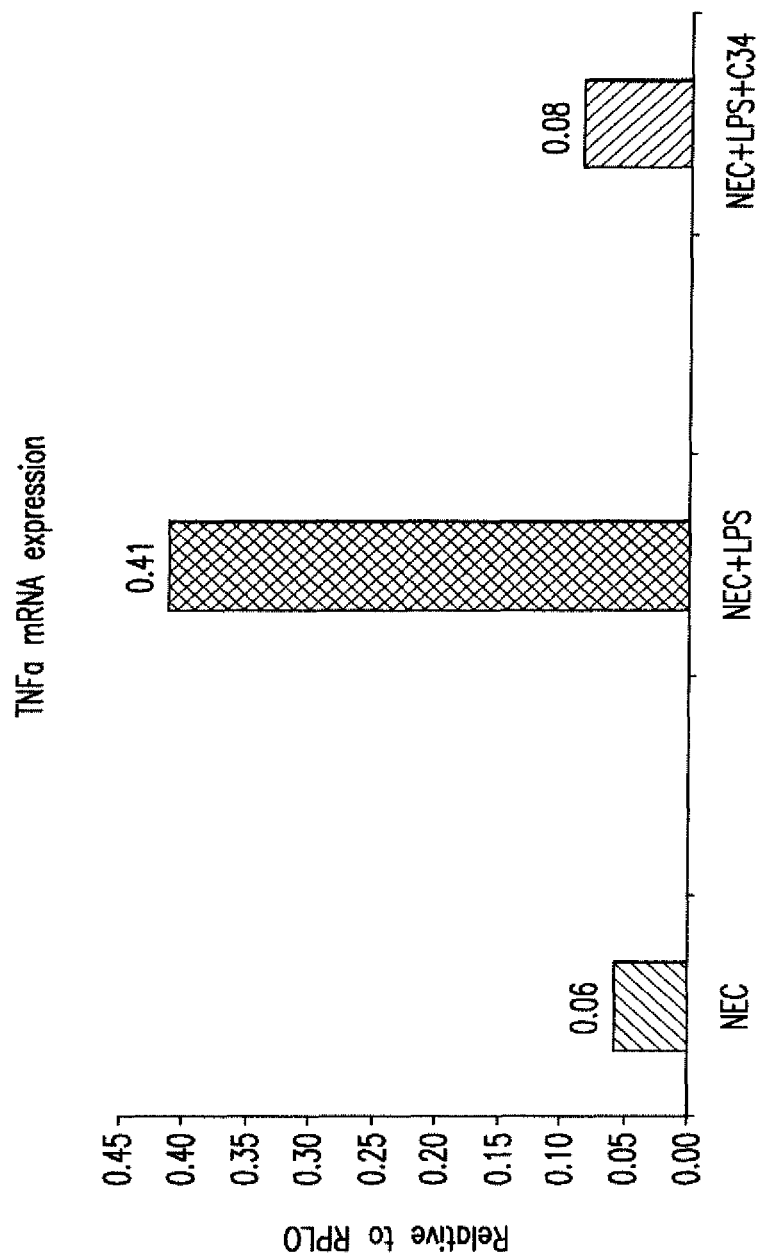

FIG. 12. TNFα mRNA levels in human NEC tissue explants treated with LPS as compared to LPS+C34.

Figure 13:
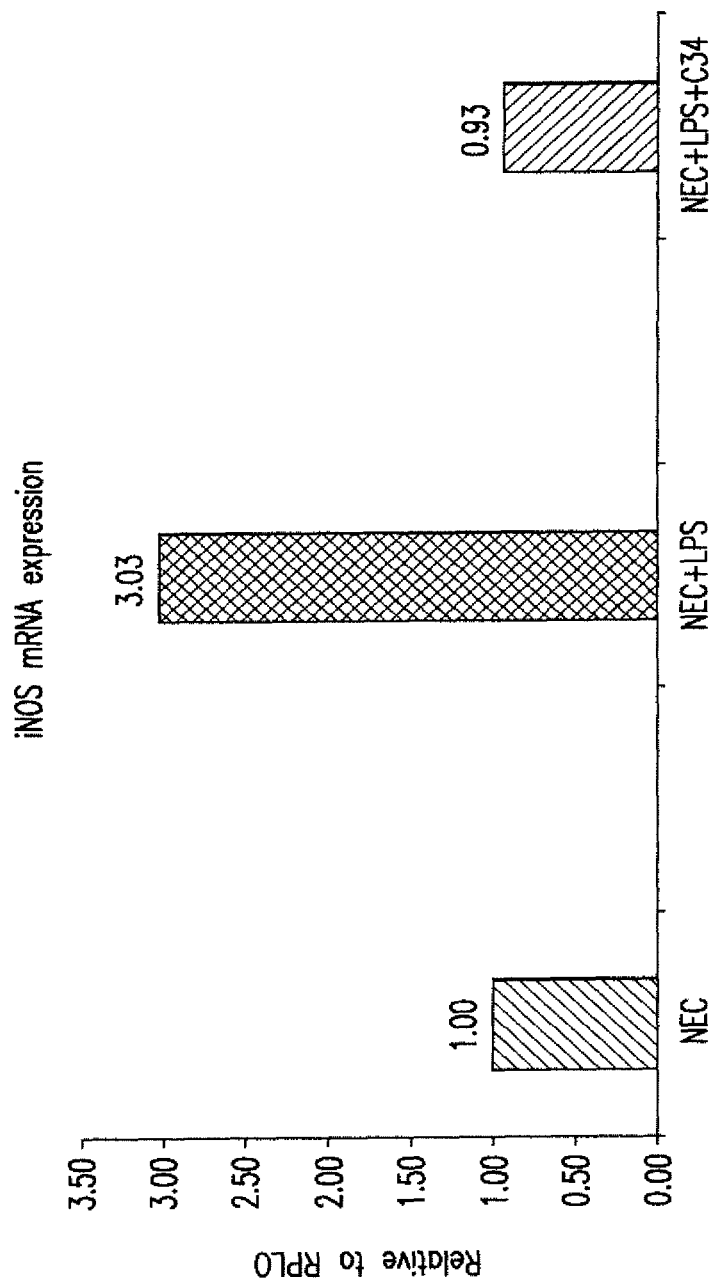

FIG. 13. iNOS mRNA levels in human NEC tissue explants treated with LPS as compared to LPS+C34.

Figure 14:
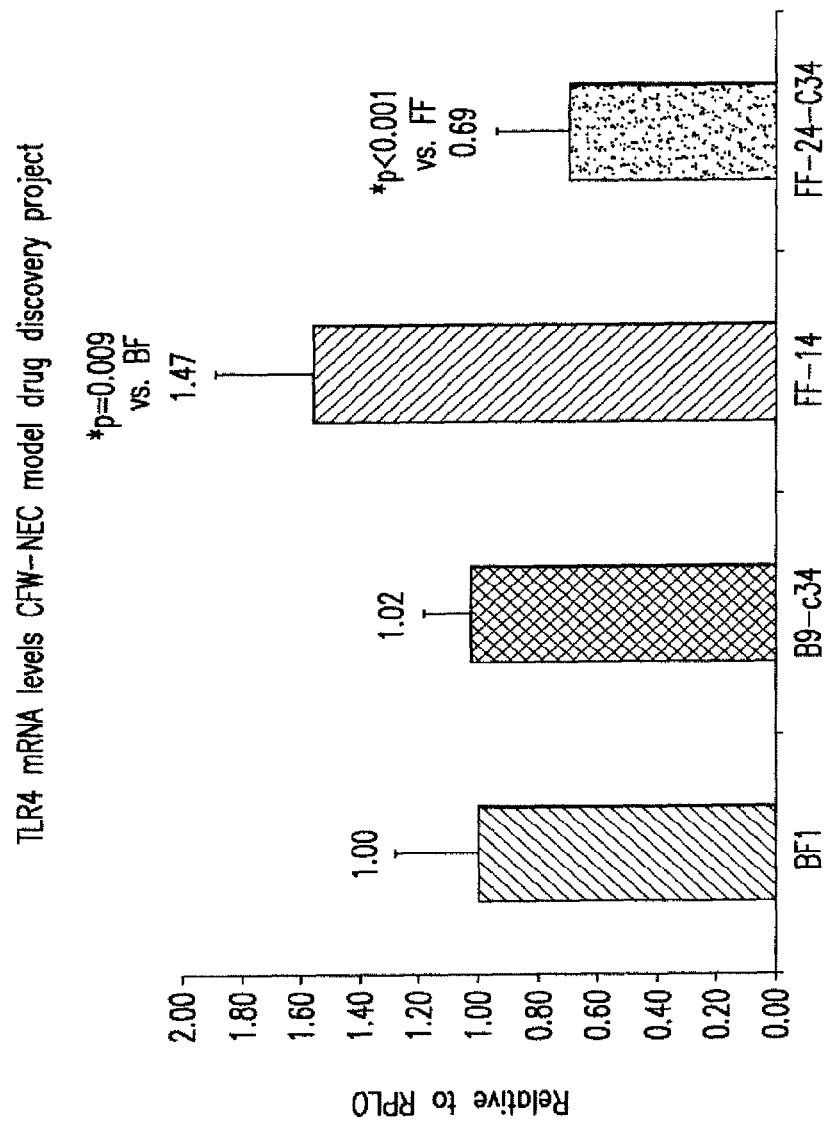

FIG. 14. TLR4 mRNA levels in breast-fed untreated or C34-treated controls as compared to formula-fed (CFW-NEC) rats that were untreated or treated with C34.

Figure 15A:
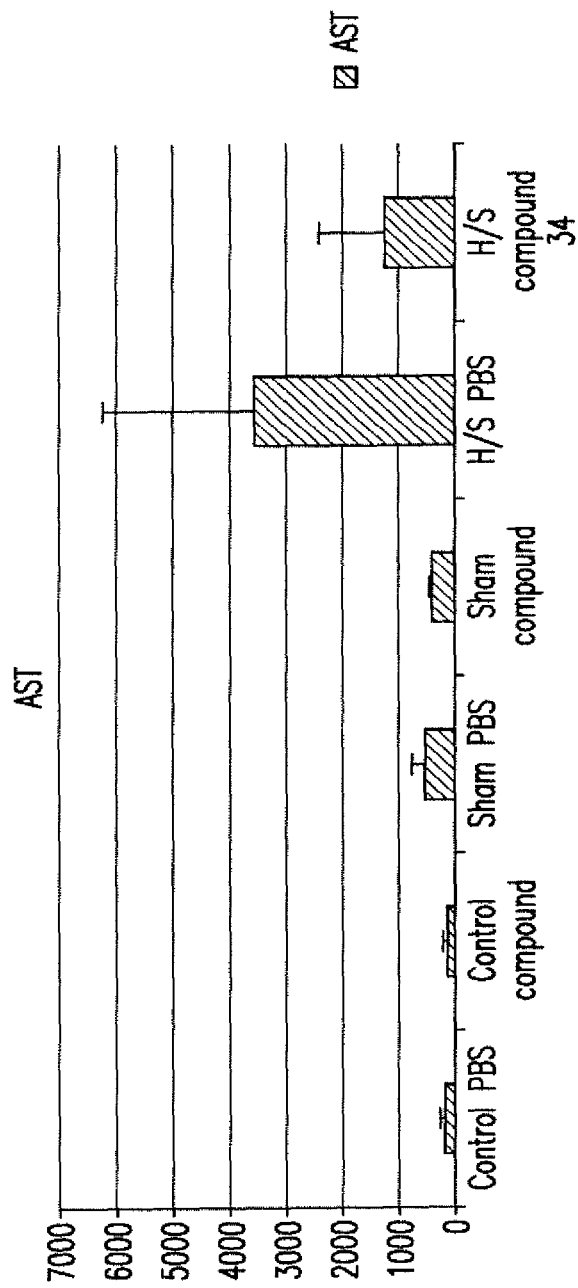
Figure 15B:
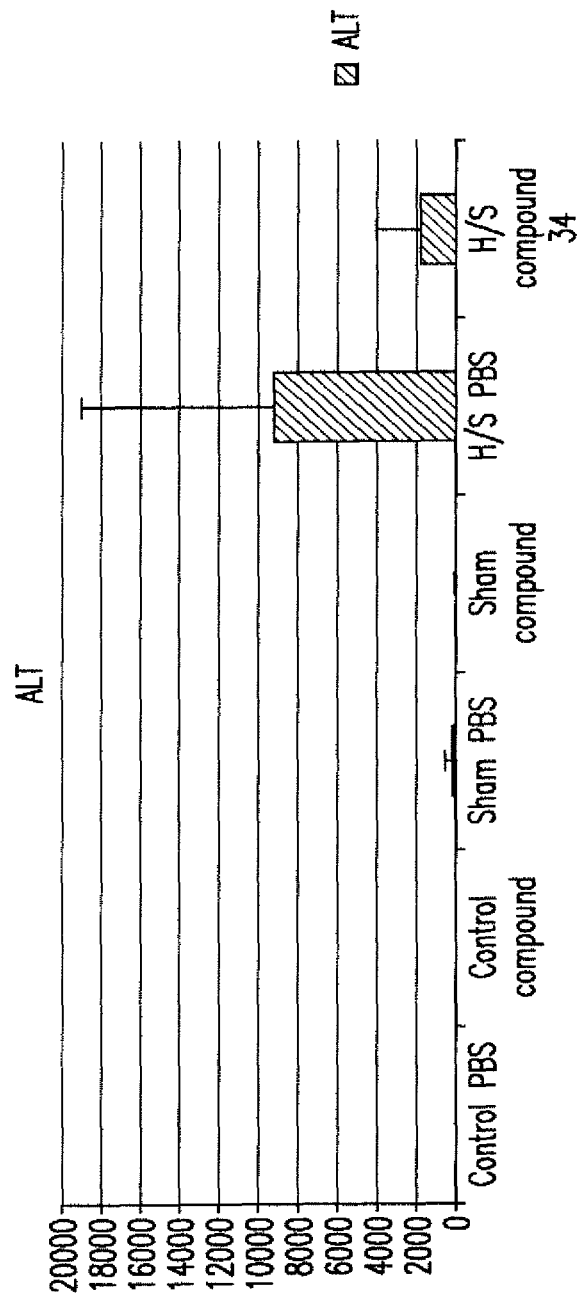

FIG. 15A-B. (A) AST levels in control animals as compared with hemorrhage-shock (H/S) model animals, and H/S animals treated with C34. ALT levels in control animals as compared with hemorrhage-shock (H/S) model animals, and H/S animals treated with C34

5. DETAILED DESCRIPTION OF THE INVENTION

For purposes of clarity and not by way of limitation, the detailed description of the invention is divided into the following subsections:

TLR4 inhibitory compounds;
(ii) pharmaceutical compositions;
(iii) disorders that may be treated; and
(iv) methods of treatment.

5.1 TLR4 Inhibitory Compounds

Compounds that may be used to inhibit TLR4 (also referred to herein as "T4ICs") according to the invention are set forth, below, in TABLE 1.

In specific, non-limiting embodiments of the invention, compounds that may be used to inhibit TLR ("T4Ics") include compounds 1, 3, 4, 5, 6, 8, 16, 21, 22, 27, 28, 29, 30, 45, and 47.

In one specific, non-limiting embodiment of the invention, the T4IC compound is compound 3, which is 4-O-(3-O-{2-(acetylamino)-2-deoxy-4-O-(6-deoxyhexopyranosyl)-3-O-[2-O-(6-deoxyhexopyranosyl)hexopyranosyl]hexopyranosyl}hexopyranosyl)hexopyranose, having the structure:

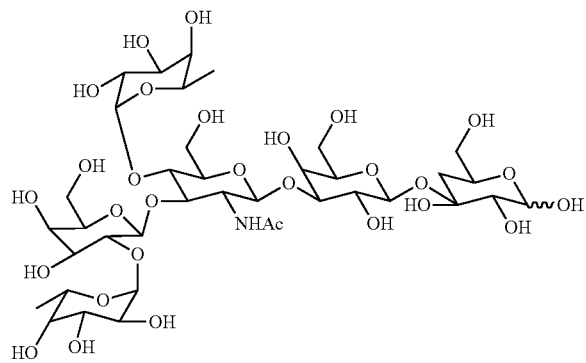 [SMILES: CC(=O)NC1C(OC2C(O)C(CO)OC(OC3(O)CC(CO)OC(O)C3O)C2O)OC(CO)C(OC2OC(C)C(O)C(O)C2O)C1OC1OC(CO)C(O)C(O)C1OC1OC(C)C(O)C(O)C1O]

In another specific, non-limiting embodiment of the invention, the T4IC compound is compound 4, which is 3-acetamido-4,5-dihydroxy-6-(hydroxymethyl)tetrahydro-2H-pyran-2-yl dihydrogen phosphate, sodium salt, having the structure:

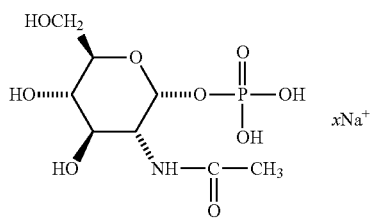

In another specific, non-limiting embodiment of the invention, the T4IC compound is compound 8, cyclohexanamine compound with 1,6-di-O-phosphono-beta-D-glycero-hexopyranose (4:1) hydrate, having the structure:

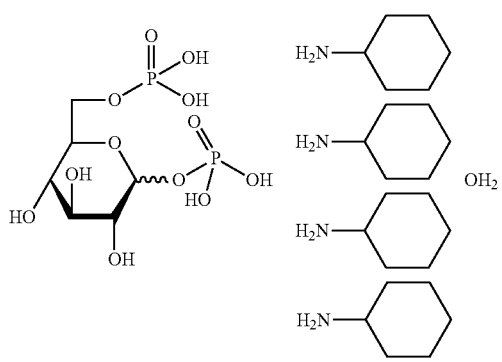

In another specific, non-limiting embodiment of the invention, the T4IC compound is compound 16, 2-(acetylamino)-2-deoxy-D-galactopyranose hydrate, having the structure:

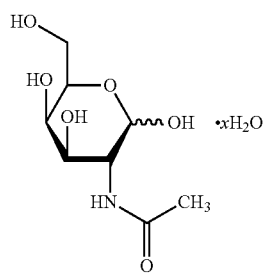

In another specific, non-limiting embodiment of the invention, the T4IC compound is compound 27, 2-(acetylamino)-2-deoxy-4-O-hexopyranosylhexopyranose, having the structure:

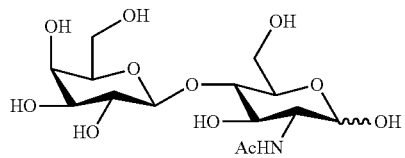

In another specific, non-limiting embodiment of the invention, the T4IC compound is compound 34, isopropyl 3,4,6-tri-O-acetyl-2-(acetylamino)-2-deoxyhexopyranoside, having the structure:

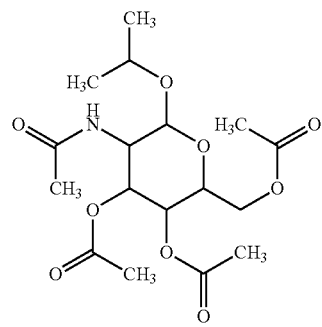 [SMILES: CC(=O)NC1C(OC(C)C)OC(COC(C)=O)C(OC(C)=O)C1OC(C)=O]

In related non-limiting embodiments, the present invention provides for derivatives of isopropyl 3,4,6-tri-O-acetyl-2-(acetylamino)-2-deoxyhexopyranoside. In one set of non-limiting embodiments, said derivatives may have FORMULA I, as follows:

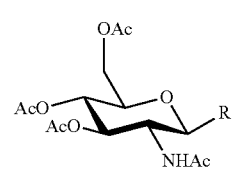

where R is selected from $R^1$ and —O—$R^1$, where $R^1$ may be a substituted or unsubstituted alkane or alkene, where the substituent if present may be methyl or ethyl, where the alkane or alkene portion optionally comprises a branched or cyclic component, and may have between 1 and 12 or between 1 and 6 carbon atoms.

In further non-limiting embodiments, said derivatives may have FORMULA II, as follows:

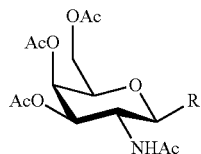

where R is selected from R¹ and —O—R¹, where R¹ may be a substituted or unsubstituted alkane or alkene, where the substituent if present may be methyl or ethyl, where the alkane or alkene portion optionally comprises a branched or cyclic component, and may have between 1 and 12 or between 1 and 6 carbon atoms.

In specific, embodiments, a derivative of isopropyl 3,4,6-tri-O-acetyl-2-(acetylamino)-2-deoxyhexopyranoside may be selected from the following group of compounds:

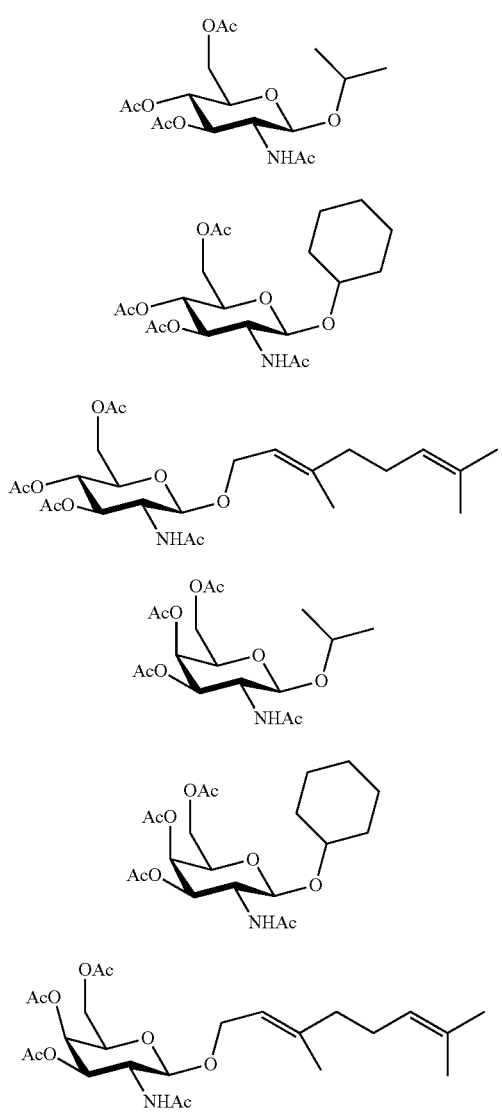

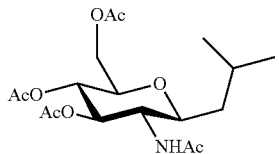

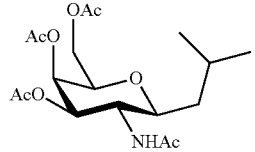

In particular non-limiting embodiments, isopropyl 3,4,6-tri-O-acetyl-2-(acetylamino)-2-deoxyhexopyranoside may be prepared by the following method:

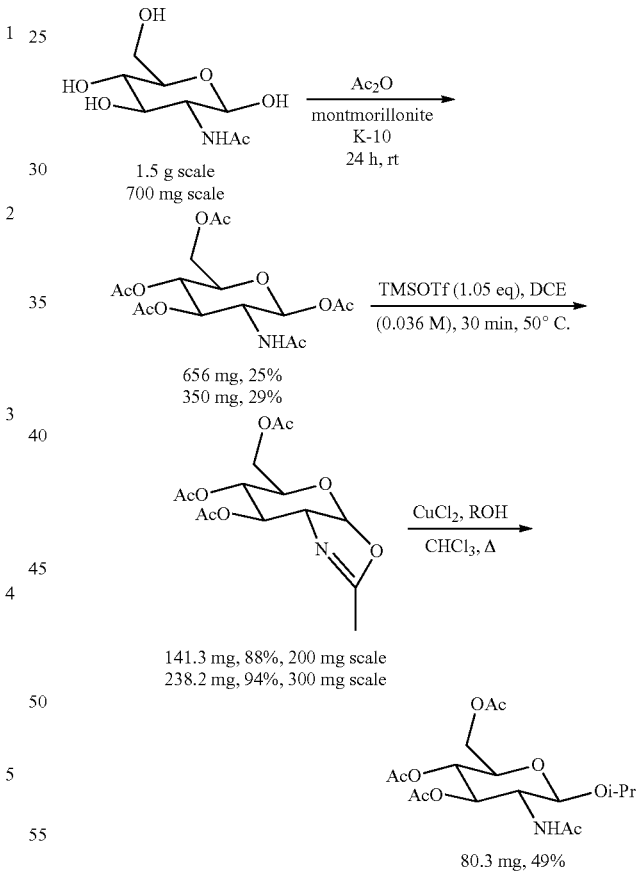

A working example containing further details of the synthesis is set forth below as section 9, Example 4, and is incorporated by reference herein.

The present invention provides for pharmaceutical compositions comprising therapeutically effective amounts of any of the foregoing compounds, for example but not limited to together with a pharmaceutical carrier such as water or other physiologic solvent. A therapeutically effective amount inhibits TLR4.

A compound is considered to inhibit TLR4 (that is, be a T4IC) if it inhibits one or preferably more sign or symptom of inflammation, such as, for example, activation of NFkB, increased expression/levels of interleukin 6 ("IL-6"), elevated erythrocyte sedimentation rate, elevated C reactive protein, fever, tachypnea, lethargy, swelling, redness, and/or pain. The ability for a compound and/or a particular concentration of a compound to inhibit TLR4 may be determined using an assay for TLR4 activity which may assess one of the abovelisted signs or symptoms. For example, TLR4 inhibition may be assayed using a method that measures the affect of a compound on NFkB activity, for example, but not limited to, the NFkB luciferase reporter mouse model, stimulated with a TLR4 ligand such as LPS, described in the example below or HEK-Blue-4 cells (InvivoGen). As other non-limiting examples of systems for testing compounds to determine TLR4 inhibitory activity, CWT mice may be treated with LPS and a test compound and monitored for signs and symptoms of inflammation, and/or C3H/WT cells (InvivoGen) may be treated with LPS and a test compound and tested for NFkB activation, IL6 production, or other markers of the inflammatory process.

5.2 Pharmaceutical Compositions

The present invention provides for pharmaceutical compositions comprising a T4IC, as described above, in a suitable pharmaceutical carrier. The amount of T4IC present in the composition may be calculated to provide, when administered to a subject in need of such treatment, an effective amount of T4IC.

In non-limiting embodiments, the T4IC may be comprised in a coated particle, micelle, liposome, or similar structure.

A pharmaceutical composition may be a liquid, comprising a T4IC in a liquid pharmaceutical carrier comprising, for example, water (an aqueous carrier) or saline. Said liquid composition may optionally further contain one or more of a buffer or a preservative.

Alternatively, a pharmaceutical composition may be a solid, for example in the form of a tablet, capsule, sachet or suppository, comprising a dose of T4IC that provides an effective amount of T4IC to a subject in need of such treatment when administered according to a dosing regimen. Said solid pharmaceutical composition may further comprise one or more excipients, for example, but not limited to, lactose, sucrose, mannitol, erythritol, carboxymethylcellulose, microcrystalline cellulose, hydroxypropylmethylcellulose, starch, polyvinylpyrrolidone, etc A pharmaceutical composition according to the invention may, in non-limiting embodiments, comprise an additional agent that may have antimicrobial and/or antiinflammatory activity, for example, but not limited to, an antibiotic agent, a steroid, or a non-steroidal antiinflammatory agent. In additional non-limiting embodiments of the invention, a pharmaceutical composition may comprise an analgesic agent. In additional non-limiting embodiments of the invention, a pharmaceutical composition may comprise an agent that improves cardiac function and/or reduces cardiac stress, for example, but not limited to, an angiotensin converting enzyme inhibitor, a beta blocker, nitroglycerin or a related nitrate compound, digoxin or a related compound, or a calcium channel blocker.

5.3 Disorders that may be Treated

The present invention may be used to treat any disease/disorder ("disorder") involving TLR4 activation, including, but not limited to, infectious diseases and inflammatory disorders such as sepsis, necrotizing enterocolitis, autoimmune diseases, Crohn's disease, celiac disease, ulcerative colitis, rheumatoid arthritis, cardiovascular disease including myocardial infarction, epilepsy, gram negative bacterial infections, aspergillosis, periodontal disease, Alzheimer's disease, cigarette smoke mediated lung inflammation, viral hepatitis (including hepatitis C virus hepatitis), alcoholic hepatitis, insulin resistance in adipocytes, and others. See, for example, United States Patent Application Publication No. US2008-0311112-A1, published Dec. 18, 2008. The present invention may also be used, in non-limiting embodiments, to treat post traumatic conditions, including ischemic injury and traumatic injury to the heart, liver, lung, kidney, intestine, brain, eye and pancreas.

5.4 Methods of Treatment

In a non-limiting embodiment, the present invention provides for a method of treating an infectious or inflammatory disorder comprising administering, to a subject in need of such treatment, an effective amount of a T4IC that reduces one or more sign or symptom of inflammation in the subject.

In another non-limiting embodiment, the present invention provides for a method of treating an intestinal inflammatory disorder in a subject comprising administering, to a subject in need of such treatment, an effective amount of a T4IC that reduces intestinal inflammation in the subject.

In another non-limiting embodiment, the present invention provides for a method of treating a cardiovascular disease in a subject comprising administering, to a subject in need of such treatment, an effective amount of a T4IC that reduces myocardial ischemia in the subject. In various non-limiting embodiments, the subject may be suffering from cardiac angina, may have suffered or is suffering a myocardial infarction, and/or may be at risk for suffering a myocardial infarction.

In another non-limiting embodiment, the present invention provides for a method of treating an inflammatory pulmonary disease in a subject comprising administering, to a subject in need of such treatment, an effective amount of a T4IC that reduces pulmonary airway inflammation in the subject.

In another non-limiting embodiment, the present invention provides for a method of treating a traumatic injury in a subject comprising administering, to a subject in need of such treatment, an effective amount of a T4IC that reduces TLR4-induced post-traumatic injury. In non-limiting embodiments, the traumatic injury is to an organ selected from the group consisting of the heart, the liver, the lung, the kidney, the intestine, the brain, the eye and the pancreas.

A subject may be a human or a non-human subject.

A T4IC may be administered by any standard route including but not limited to oral, intraperitoneal (i.p), intravenous (i.v.), subcutaneous (s.c.), intradermal, intramuscular (i.m.) intraarticular, intrathecal, intraarterial, intravaginal, rectal, nasal, pulmonary, etc.

An effective dose may be determined using methods known in the art (including but not limited to TLR4 activity assays described herein). In specific, non-limiting embodiments of the invention, an effective dose may be between about 0.01 and 50 micromoles of T4IC per kilogram weight of the subject, or between about 0.1 and 20 micromoles of T4IC per kilogram weight of the subject. In specific, non-limiting embodiments, the dose of T4IC may be between about 0.001 and 100 milligrams per kilogram weight of the subject, or between about 0.01 and 10 milligrams per kilogram weight of the subject, or between about 0.1 and 10 milligrams per kilogram weight of the subject, or between about 0.5 and 5 milligrams per kilogram weight of the subject.

6. EXAMPLE 1

6.1 Materials and Methods

In Silico Similarity Screen.

In order to identify inhibitors of TLR4, the structure of a known TLR4 inhibitor, E5564, was utilized. E5564 is a second-generation synthetic analogue of the lipid A component of endotoxin (lipopolysaccharide [LPS]). Based on the published structure of E5564, an in silico similarity screen was conducted using the on-line iResearch library of Chem-Navigator (San Diego, Calif.) accessed at www.chemnavigator.com. This compound library was chosen to maximize structural diversity while including drug-like structures, and also to include multiple Food and Drug Administration-approved drugs, known bioactive compounds, metabolites, natural products and related compounds.

Compound Preparation and Delivery.

All 65 identified compounds were received in solid form and stored at 4° C. until use. Stock solutions of each compound were made by dissolving the appropriate amount of each compound in dimethyl sulfoxide (DMSO) to yield a concentration of 10 mM. Immediately prior to injection into experimental animals, the compounds were diluted to an experimental concentration of 100 uM in phosphate-buffered saline (PBS). Total concentration of DMSO in the final diluted drug was 1%. Compounds were closely examined to insure that no precipitate formed prior to injection and were stored on ice until injection. All compounds were given via intraperitoneal (i.p.) injection in a total volume of 200 ul using a 1 cc syringe and 27 gauge needle. In all experiments listed below, the compounds were delivered to the experimental mice 30 minutes prior to injection with lipopolysaccharide (LPS) to induce endotoxemia. Control animals not receiving compound received 1% DMSO dissolved in PBS. Following drug injection, the mice were observed closely in their cages for signs of immediate toxicity or adverse reaction to the drug, including but not limited to piloerection, tachypnea, bleeding, abnormal or aggressive behavior, signs of altered mental status, and level of activity.

Induction of Endotoxemia.

All mice were housed and cared for at the Rangos Research Center, Children's Hospital of Pittsburgh (Pittsburgh, Pa.). All experiments were approved by the Children's Hospital of Pittsburgh Animal Care Committee and by the Institutional Review Board of the University of Pittsburgh. Swiss Webster (CFW) and NFkB-luciferase reporter mice were obtained from The Jackson Laboratory. Throughout the course of all experiments, mice were housed 4 per cage with access to food, water, and standard bedding. Endotoxemia was induced in all experiments by i.p. injection of LPS (*Escherichia coli* 0111:B4 purified by gel filtration chromatography, >99% pure, Sigma-Aldrich) at a dose of 2 mg/kg for 6 hours. At the end of each experiment, all animals were euthanized by $CO_2$ hypoxia and cervical dislocation.

Two separate in vivo experimental designs were utilized to assess the effect of pretreatment with each individual compound in a model of endotoxemia. The first series of experiments involved the use of the NFkB reporter mice, while the second utilized CFW.

NFkB-Luciferase Reporter Mice Assay.

NFkB-luciferase reporter mice, in which the NFkB is downstream of the luciferase gene, were subjected to endotoxemia with or without pretreatment with experimental compounds. The experimental compounds treated by this assay were compounds 1-6, with compounds 1-3 tested first and compounds 4-6 tested later. For both experiments, the mice were 6 weeks old on the date of the experiment. Controls for each included 1% DMSO alone, LPS alone (2 mg/kg, 6 hrs), and pretreatment with the known NFkB inhibitor Bay-11-7082 (20 mg/kg, 30 minute pretreatment via i.p. injection, Cayman Chemical). Following 6 hours of endotoxemia, each mouse was given an i.p. injection of luciferin (160 ug/kg, Invitrogen), then after 10 minutes a whole animal image was obtained using the IVIS Lumina 3D Optical in vivo imaging system (Caliper Life Sciences, Hopkinton, Mass.) under 1.5% isofluorane anesthesia. After whole body imaging, an additional injection of luciferin is given and animals were euthanized, organs were harvested, and the extent of NFkB activation within various tissues was further analyzed by an additional luminescence image of the individual organs.

CFW Endotoxemia Assay.

In order to effectively screen the entire compound list, the remaining compounds (7-60) were screened in a model of endotoxemia using CFW mice. Three separate experiments were performed: First, Compound 7 along with a repeat of compound 4 (n=3 mice per compound, mice age 5 weeks) were tested. Controls were saline injection alone (n=1), LPS 2 mg/kg 6 hrs (n=2). Second, compounds 3, 4, 6, 8-32 were tested (n=1 mouse each, 3 week old mice). Controls were saline injection alone (n=1), LPS 2 mg/kg 6 hrs (n=2), LPS 10 mg/kg 6 hrs (n=2), Bay 11 pretreatment 20 mg/kg for 30 minutes prior to LPS 2 mg/kg 6 hrs. Third, compounds 8, 16, 33-60 were tested (n=1 mouse each, 3 week old mice). Controls were saline injection alone (n=1), LPS 2 mg/kg 6 hrs (n=2), Bay 11 pretreatment 20 mg/kg for 30 minutes prior to LPS 2 mg/kg 6 hrs. Following 6 hours of endotoxemia, mice from the second and third experiments were observed within their cages and videotaped to document behavior and phenotypic differences to assess for an inhibitory effect of compound pretreatment on the effects of LPS. Mice were identified by a number previously placed using permanent marker on their tails. The degree of piloerection, tachypnea, location in the cage (center of cage versus corners), degree of activity, and behavior relative to other animals was observed and documented via video for each mouse.

Enzyme Linked Immunosorbent Assay (ELISA).

Prior to being euthanized, mice from the NFkB luciferase and all three CFW endotoxemia experiments were anesthetized (1.5% isofluorane) and a retro-orbital sinus puncture was performed to obtain a blood sample. Serum was obtained via centrifugation and an ELISA was performed to assess for IL-6 expression using a pre-made kit (R&D Biosystems). Results are reported relative to a standard curve for each experiment as pg/ml.

6.2 Results

With a view to identifying TLR4 inhibitors amongst previously known compounds (that were not hitherto known to have TLR4 inhibitory activity), a library of compounds was screened for those bearing structural similarity to the known TLR4 inhibitor, E5564. A total of 124,413,264 samples within the library were screened, and a total of 100 structures were identified with a similarity greater than 70%. Excluding the known TLR4 agonist, LPS, which was identified in the search, the remaining 99 compounds were then researched for commercial availability. A total of 65 commercially available compounds were identified and obtained in amounts ranging from 1-100 mg from ChemNavigator. These 65 compounds are shown in TABLE 1. Compounds 9, 10, 11, 13, 14, 17, 21, 33 and 35-39 are available from InterBioScreen Ltd., compounds 3, 5, 6, 8, 23, 30 and 49-58 are available from Carbosynth Ltd., compounds 12, 22, 24 and 34 are available from Enamine, compound 59 is available from Synthon Lab Ltd., compounds 1, 4, 7, 15, 16, 18, 19, 32, 40, 41 and 60 are available from Sigma-Aldrich, compounds 42 and 43 are available from Bosche Scientific LLC, compounds 2, 20, 25, 26, 27, 44, 45, 47 and 48 are available from Toronto Research Chemicals, compound 65 is available from PBMR Labs, Ukraine, compounds 31 and 46 are available from Maybridge Ltd., compound 28 is available from Labotest and compounds 29 and 61-64 are available from CehDiv Inc.

TABLE 1

| Compound ID | IUPAC Name | Stock number |
|---|---|---|
| 11 | (2S-2-((4aR,6R,7R,8R,8aS)-7-acetamido-6-(2,3-bis(dodecyloxy)propoxy)-2,2-dimethylhexahydropyrano[3,2-d][1,3]dioxin-8-yloxy)propanoic acid | 2010749 |
| 33 | dodecyl 3,4,6-tri-O-acetyl-2-(acetylamino)-2-deoxy-beta-D-glucopyranoside | 2010752 |
| 14 | butyl 2-(acetylamino)-2-deoxy-3,4-di-O-methyl-beta-D-glucopyranoside | 2010750 |
| 34 | isopropyl 3,4,6-tri-O-acetyl-2-(acetylamino)-2-deoxyhexopyranoside | 2010760 |
| 35 | cyclohexyl 3,4,6-tri-O-acetyl-2-(acetylamino)-2-deoxy-alpha-D-glucopyranoside | 2010748 |
| 36 | hexyl 3,4,6-tri-O-acetyl-2-(acetylamino)-2-deoxy-beta-D-glucopyranoside | 2010747 |
| 37 | N-[(2R,3R,4R,5S,6R)-2-[(1'S,2'R,6'R,8'R,9'S)-dispiro[cyclohexane-1,4'-[3, 5, 7, 10, 12]pentaoxatricyclo[7.3.0.0^{2,6}]dodecane-11'1''-cyclohexane]-8'-ylmethoxy]-4,5-dihydroxy-6-(hydroxymethyl)oxan-3-yl]acetamide | 2010754 |
| 38 | (2R,3S,4R,5R,6R)-5-acetamido-2-(acetoxymethyl)-6-(((3aR, 5R, 5aS, 8aS, 8bR)-2,2,7,7-tetramethyltetrahydro-3aH-bis[1,3]dioxolo[4,5-b:4'5'-d]pyran-5-yl)methoxy)tetrahydro-2H-pyran-3,4-diyl-diacetate | 2010753 |
| 21 | N-((2R,3R,4R,5S,6R)-4,5-dihydroxy-6-(hydroxymethyl)-2-(((3aR,5R,5aS,8aS,8bR)-2,2,7,7-tetramethyltetrahydro-3aH-bis[1,3]dioxolo[4,5-b:4',5'F27-d]pyran-5-yl)methoxy)tetrahydro-2H-pyran-3-yl) acetamide | 2010759 |
| 12 | propyl 3,4,6-tri-O-acetyl-2-(acetylamino)-2-deoxyhexopyranoside | 2010761 |
| 24 | 1,3,4,6-tetra-O-acetyl-2-deoxy-2-(palmitoylamino)hexopyranose | 2010762 |
| 10 | 6-O-[2-(acetylamino)-2-deoxy-beta-D-glucopyranosyl]-3-O-isopentyl-1,2-O-(1-methylethylidene)-alpha-D-xylo-hexofuranose | 2010757 |
| 39 | 6-O-[2-(acetylamino)-2-deoxy-beta-D-glucopyranosyl]-1,2-O-(1-methylethylidene)-3-O-propyl-alpha-D-xylo-hexofuranose | 2010758 |
| 17 | 1,2-O-(1-methylethylidene)-3-O-propyl-6-O-[3,4,6-tri-O-acetyl-2-(acetylamino)-2-deoxy-beta-D-glucopyranosyl]-alpha-D-xylo-hexofuranose | 2010755 |
| 9 | 1,2-O-(1-methylethylidene)-3-O-pentyl-6-O-[3,4,6-tri-O-acetyl-2-(acetylamino)-2-deoxy-beta-D-glucopyranosyl]-alpha-D-xylo-hexofuranose | 2010756 |
| 13 | octyl 2-(acetylamino)-2-deoxy-beta-D-glycero-hexopyranoside | 2010751 |
| 22 | sec-butyl 2-(acetylamino)-2-deoxyhexopyranoside | 2010763 |
| 19 | (2S,4S,5R,6R)-5-acetamido-2-((2R,3S,4S,5R,6S)-3,5-dihydroxy-2-(hydroxymethyl)-6-((2R,3S,4R,5S)-4,5,6-trihydroxy-2-(hydroxymethyl)tetrahydro-2H-pyran-3-yloxy) | 2010745 |
| 32 | sodium (2S,3S,4R,5R,6R)-3-((2S,3R,5S,6R)-3-acetamido-5-hydroxy-6-(hydroxymethyl)tetrahydro-2H-pyran-2-yloxy)-4,5,6-trihydroxytetrahydro-2H-pyran-2-carboxylate | 2010739 |
| 1 | 2-(acetylamino)-4-O-{2-(acetylamino)-4-O-[2-(acetylamino)-2-deoxy-beta-D-glucopyranosyl]-2-deoxy-beta-D-glucopyranosyl}-2-deoxy-D-glucopyranose | 2010744 |
| 4 | 3-acetamido-4,5-dihydroxy-6-(hydroxymethyl)tetrahydro-2H-pyran-2-yl dihydrogen phosphate, sodium salt | 2010742 |
| 15 | sulfuric acid compound with (2R)-4-amino-N-{(1R,2S,3S,4R,5S)-5-amino-2-[(3-amino-3-deoxy-alpha-D-glucopyranosyl)oxy]-4-[(6-amino-6-deoxy-alpha-D-glucopyranosyl)oxy]-3-hydroxycyclohexyl}-2-hydroxybutanamide (1:1) | 2010737 |
| 40 | (4R)-4-((2S)-2-((2R)-2-((3R,4R,5S,6R)-3-acetamido-2,5-dihydroxy-6-(hydroxymethyl)tetrahydro-2H-pyran-4-yloxy)propanamido)propanamido)-5-amino-5-oxopentanoic acid | 2010746 |

TABLE 1-continued

| Compound ID | IUPAC Name | Stock number |
|---|---|---|
| 41 | Uridine 5'-diphospho-N-acetylglucosamine sodium salt | 2010741 |
| 18 | Uridine 5'-diphospho-N-acetylgalactosamine disodium salt | 2010743 |
| 42 | 2-(acetylamino)-3-O-{4-O-[2-(acetylamino)-2-deoxy-3-O-alpha-D-xylo-hexopyranuronosyl-beta-D-ribo-hexopyranosyl]-beta-D-xylo-hexopyranuronosyl}-2-deoxy-D-glucopyranose | 2010792 |
| 43 | 2-(acetylamino)-2-deoxy-3-O-(6,8-dideoxy-beta-L-glycero-octopyranosyl-7-ulose)-4-O-sulfo-L-erythro-hexopyranose | 2010793 |
| 27 | 2-(acetylamino)-2-deoxy-4-O-hexopyranosylhexopyranose | 2010777 |
| 2 | N-{(1S,2S,3R)-1-[(beta-L-glycero-hexopyranosyloxy)methyl]-2,3-dihydroxyheptadecyl}hexacosanamide | 2010778 |
| 25 | dimethyl 5-(acetylamino)-3,5-dideoxy-D-erythro-non-2-ulopyranosidonate | 2010764 |
| 20 | methyl 2-(acetylamino)-2-deoxy-3-O-hexopyranosylhexopyranoside | 2010776 |
| 44 | 8-{[2-(acetylamino)-4-O-[2-(acetylamino)-2-deoxyhexopyranosyl]-2-deoxy-6-O-(6-deoxyhexopyranosyl)hexopyranosyl]oxy}octyl acetate | 2010781 |
| 26 | octyl 2-(acetylamino)-2-deoxyhexopyranoside | 2010775 |
| 45 | 2-(acetylamino)-2-deoxy-4-O-(6-deoxyhexopyranosyl)-3-O-hexopyranosylhexopyranose | 2010774 |
| 31 | 2-(acetylamino)-2-deoxy-alpha-D-lyxo-hexopyranose | 2010772 |
| 46 | 2-(acetylamino)-2-deoxy-D-glucopyranose | 2010773 |
| 47 | allyl 3,4,6-tri-O-acetyl-2-(acetylamino)-2-deoxy-beta-D-lyxo-hexopyranoside | 2010780 |
| 48 | N-{(1S,2R,3E)-1-[(beta-L-ribo-hexopyranosyloxy)methyl]-2-hydroxy-3-heptadecenyl}octadecanamide | 2010779 |
| 49 | sodium ((3S,6R)-5-acetamido-3,4,6-trihydroxytetrahydro-2H-pyran-2-yl)methyl phosphate | 2010787 |
| 30 | 2-((2R,5S)-3-acetamido-2,5-dihydroxy-6-(hydroxymethyl)tetrahydro-2H-pyran-4-yloxy)propanoic acid | 2010782 |
| 50 | allyl 2-(acetylamino)-2-deoxy-beta-D-glycero-hexopyranoside | 2010765 |
| 51 | 1,3,4,6-tetra-O-acetyl-2-(acetylamino)-2-deoxy-beta-D-glycero-hexopyranose | 2010766 |
| 52 | 2-(acetylamino)-2-deoxy-beta-D-glycero-hexopyranose | 2010769 |
| 53 | 4-O-[2-(acetylamino)-2-deoxyhexopyranosyl]-1,5-anhydro-2-deoxyhexitol | 2010791 |
| 54 | ethyl 2-(acetylamino)-2-deoxy-beta-D-glycero-hexopyranoside | 2010785 |
| 55 | ethyl 3,4,6-tri-O-acetyl-2-(acetylamino)-2-deoxy-beta-D-glycero-hexopyranoside | 2010784 |
| 5 | 5-acetamido-6-((1R,2R>)-3-(3-(3-acetamido-5-hydroxy-6-(hydroxymethyl)-4-(3,4,5-trihydroxy-6-(hydroxymethyl)tetrahydro-2H>-pyran-2-yloxy)tetrahydro-2H-pyran-2-yloxy)-6-(4,5-dihydroxy-6-((E)-3-hydroxy-2-stearamidooctadec-4-e | 2010770 |
| 8 | cyclohexanamine compound with 1,6-di-O-phosphono-beta-D-glycero-hexopyranose (4:1) hydrate | 2010788 |
| 3 | 4-O-(3-O-{2-(acetylamino)-2-deoxy-4-O-(6-deoxyhexopyranosyl)-3-O-[2-O-(6-deoxyhexopyranosyl)hexopyranosyl]hexopyranosyl}hexopyranosyl)hexopyranose | 2010789 |
| 6 | 3-O-(3-O-{2-(acetylamino)-2-deoxy-3-O-[2-O-(6-deoxyhexopyranosyl)hexopyranosyl]hexopyranosyl}hexopyranosyl)-D-arabinose | 2010783 |
| 23 | 2-(acetylamino)-2-deoxy-3-O-(6-deoxyhexopyranosyl)-4-O-hexopyranosylhexopyranose | 2010790 |
| 56 | nonyl 2-(acetylamino)-2-deoxy-beta-D-glycero-hexopyranoside | 2010767 |
| 57 | octadecyl 2-(acetylamino)-2-deoxy-beta-D-glycero-hexopyranoside | 2010768 |
| 58 | 4-O-{6-O-[5-(acetylamino)-3,5-dideoxy-D-erythro-non-2-ulopyranonosyl]hexopyranosyl}hexopyranose | 2010786 |
| 59 | 2-deoxy-2-(propionylamino)-D-glucopyranose | 2010771 |
| 7 | cyclohexane-1,2,3,4,5,6-hexayl hexakis(dihydrogen phosphate), magnesium potassium salt | 2010736 |
| 60 | 1,3,4,6-tetra-O-acetyl-2-(acetylamino)-2-deoxy-beta-D-glucopyranose | 2010738 |
| 16 | 2-(acetylamino)-2-deoxy-D-galactopyranose hydrate | 2010740 |
| 28 | [(4R)-5-acetamido-3,4,6-triacetyloxy-oxan-2-yl]methyl acetate | 2017191 |
| 61 | [5-acetamido-3-acetyloxy-2-(acetyloxymethyl)-6-hexadecoxy-oxan-4-yl]acetate | 2017186 |
| 29 | (5-acetamido-3,4-diacetyloxy-6-pentoxy-oxan-2-yl)methyl acetate | 2017187 |
| 62 | (5-acetamido-3,4-diacetyloxy-6-methoxy-oxan-2-yl)methyl acetate | 2017188 |
| 63 | N-[2-ethoxy-4,5-dihydroxy-6-(hydroxymethyl)oxan-3-yl]acetamide | 2017189 |
| 64 | [2,5-diacetyloxy-6-(acetyloxymethyl)-3-(dodecanoylamino)oxan-4-yl] acetate | 2017190 |
| 65 | N-[2-(dispiro[BLAH]ylmethoxy)-4,5-dihydroxy-6-(hydroxymethyl)oxan-3-yl]acetamide | 2017192 |

Next, 60 of the 65 compounds were tested to determine whether they exhibit TLR4 inhibitory activity in a murine LPS-induced model for endotoxemia. The first series of experiments involved the use of the NFkB luciferase reporter mice (testing compounds 1-6), while the second utilized CFW mice (testing compounds 3-65). In all cases, each mouse received 20 nanomoles of test compound, or approximately 1 micromole per kilogram weight.

The results of the studies in NFkB luciferase reporter mice are shown in FIGS. 1-8; FIGS. 1-7 are photographs generated by the IVIS Lumina 3D Optical in vivo imaging system, and FIG. 8A-B are bar graphs summarizing the results. Bay-11-7082 was used as a positive control for TLR4 inhibitory activity. These results indicate that, at the concentration tested, with the exception of compound 2, the other putative TLR inhibitors 1 and 3-6 all inhibited LPS-induced NFkB activation to some extent, with compound 4 having the greatest inhibitory activity in this assay.

The results of the study of compounds 3-65 in the CFW endotoxemia model are presented in TABLE 2 below. Less activity, tachypnea, and piloerection are considered symptomatic of endotoxemia, so a decrease in these is consistent with TLR inhibition by the administered compound. Note that compunds listed as negatives may still be T4Ics at other concentrations or conditions.

TABLE 2

| Observation | |
|---|---|
| Compound "Hits" | |
| 3* | More active, remained in center rather than huddling in corner, less tachypneic, sniffing and crawling over other affected mice in cage |
| 4* | Appears similar to saline, robust activity, self grooming and very active |
| 8* | More mobile, less piloerection |
| 16* | Nearly appeared unaffected, no piloerection obvious, very active, minimal tachypnea |
| 21 | More active, crawled over other mice, less piloerection |
| 27* | Less piloerection, less tachypnea, scattered when top of cage removed, jumping and moving throughout the cage unstimulated |
| 29 | More mobile, less piloerection, less tachypnea, scattered when top of cage removed |
| 30 | Less tachypnea, more mobile |
| 34* | Similar activity to C27, much more active, less tachypnea |
| 35 | More mobile, less piloerection, less tachypnea, scattered when top of cage removed |
| 36 | More active, crawled over other mice, less piloerection |
| 42 | Less tachypnea, more mobile |
| 43 | More active, crawled over other mice, less piloerection |
| 45 | More active, crawled over other mice, less piloerection |
| 47 | More active, crawled over other mice, less piloerection |
| 50 | More active |
| 52 | More active, less piloerection |
| 54 | Less piloerection, less tachypnea |
| 55 | Less piloerection, less tachypnea, more active |
| 61 | Less piloerection, less tachypnea |
| 63 | More mobile, less piloerection |
| Compound "Negatives" | |
| 1 | More tachypnea, rigors |
| 5* | Little activity, huddled in corner, very tachynpeic, no resistance to being handled |
| 14 | Refused to move from corner, very tachpneic |
| 25 | More piloerection, less mobile than other in the cage |
| 31 | More tachypneic, more piloerection |
| 32 | More tachypneic, more piloerection |
| 37 | More tachypneic, less active |
| 38 | Less active |
| 40 | Less active, huddled in corner |

TABLE 2-continued

| Observation | |
|---|---|
| 41 | Less active, huddled in corner |
| 62* | Nearly static, little movement, rigors |

*Indicates most profound phenotypic differences from each group (positive or negative).

7. EXAMPLE 2

Experiments were performed to further explore the activity of certain "positive" TLR4 inhibitors described in TABLES 1 and 2.

In a first set of experiments, NFκB luciferase reporter mice, as described above, in which NFκB is downstream of the luciferase gene, were treated with either (i) saline (FIG. 10A, animal on the left); (ii) LPS alone (2 mg/kg; FIG. 10A, animal on the right)); (iii) LPS plus C16 ((1 mg/kg, intraperitoneal (i.p.) injection); FIG. 10B, animal on the left) or (iv) LPS plus C34 ((1 mg/kg, i.p. injection); FIG. 10B, animal on the right). As the amount of luciferase reflects NFκB signalling, the imaging studies indicate that both compounds C16 and C34 reduced NFκB signalling.

Inducible nitric oxide synthase (iNOS) is associated with necrotizing enterocolitis (NEC) in human infants. In a second set of experiments, the CFW-NEC mouse model system for NEC was used to evaluate the effect of various compounds from TABLES 1 and 2 above on iNOS mRNA levels. A model system for NEC was induced in newborn mouse pups by formula feeding, where control animals were breast-fed (Sodhi et al., 2010, Gastroenterol. 138(1):185-196; Richardson et al., 2010, Gastroenterol. 139(3):904-917). As shown in FIG. 11, the level of iNOS was substantially increased in the formula-fed (FF) group. This increase was much less when FF pups were also administered C27 (1 mg/kg, i.p., once daily for the first four days of the five day model) and the increase was almost eliminated by C34 (1 mg/kg, i.p., once daily for the first four days of the five day model). Note that RPLO stands for 50S ribosomal subunit protein L15, an acknowledged housekeeping gene, which means that it is a constitutive gene expressed at relatively constant levels by all cells and is thus used as a reference for comparing other genes which may vary under experimental conditions. In this same model system, levels of TLR4 mRNA levels were also evaluated. The level of TLR4 mRNA seen in breast-fed animals, including breast-fed animals treated with C34, was substantially increased in the FF animals. In contrast, the level of TLR4 was not increased in FF animals treated with C34 (1 mg/kg, i.p. once daily for the first four days of the five day model) and indeed mRNA levels were 30 percent below normal (see FIG. 14).

The effect of C34 was then tested on explants of human NEC tissue. These explants were obtained from human infants suffering from NEC and were prepared from NEC-affected portions of the intestine. When explants were treated with LPS (25 ug/ml, 37° C., 3 hours) the level of TNFα mRNA (FIG. 12) and iNOS mRNA (FIG. 13) increased precipitously. These increases were substantially reduced by treatment with C34 (10 uM, tissue was pretreated for 30 minutes prior to LPS being added; C34 was not removed and remained in solution during incubation with LPS; FIGS. 12 and 13).

All the foregoing data supports the use of compounds C34, C16 and C27 as TLR4 inhibitors, as inhibitors of inflammation, and as inhibitors and agents for treatment of NEC.

8. EXAMPLE 3

An experiment was performed to test the effect of TLR4 inhibitors and C34 in particular on the tissue damage associated with hemmorhagic shock. A murine model was used in which, under sterile conditions and anesthesia induced using i.p. sodium pentobarbital (20 mg/kg), a left groin exploration was performed, and the left femoral artery was cannulated with tapered polyethylene (PE)-10 tubing and connected to a blood pressure transducer for continuous mean arterial pressure (MAP) monitoring for the duration of the experiment (6 h) as described in Sodhi, et al., 2011, Am. J. Physiol. Gastrointest. Liver Physiol. 300(5):G862-G873. To induce hemorrhagic shock, blood was withdrawn to allow the mean arterial pressure to drop to 25 mmHg over 5 minutes, and the blood pressure was maintained at this level for 150 min. The mice were then resuscitated over 10 min with lactated Ringer's solution. Sham-operated mice underwent anesthesia and femoral cannulation only. In this model system, the extent of liver damage is reflected in increased serum levels of aspartate aminotransferase (AST) and alanine transaminase (ALT). As shown in FIG. 15A-B, administration of C34 (1 mg/kg, i.p. divided in two doses with one given 30 minutes prior to H/S and the second given immediately prior to resuscitation) inhibited the increases in AST (FIG. 15A) and ALT (FIG. 15B) observed in H/S animals receiving phosphate buffered saline (PBS), supporting the effectiveness of compound C34 in reducing the extent of tissue damage/injury associated with trauma and/or shock.

9. EXAMPLE 4

Synthesis of Isopropyl 3,4,6-tri-O-acetyl-2-(acetylamino)-2-deoxyhexopyranoside (C34)

2-Acetamido-2-deoxy-1,3,4,6-tetra-O-acetyl-β-D-glucopyranose

A dry, 100 mL round-bottom flask was equipped with a Teflon coated stir bar, septum and an ice-salt bath. The flask was put under an argon atmosphere and acetic anhydride (8.40 g, 7.76 mL, 82.27 mmol) which was stored in the freezer at 5° C. was added via syringe. The acetic anhydride was cooled for 15 min at 0° C. After 15 min, the septum was replaced with a funnel and N-acetyl-D-glucosamine (0.692 g, 3.13 mmol) and montmorillonite K-10 (2.4 g) were added sequentially and slowly over 15 min. The stopper was then replaced the ice bath removed and the reaction was stirred for 24 hours. The reaction mixture was then filtered through a medium porosity sintered glass funnel precoated with a pad of celite moistened by methyl acetate. The flask and filtered solids were rinsed with methyl acetate (100 mL) and the combined filtrate was concentrated under rotary evaporation (40° C.). The resulting orange residue was dislodged with a spatula and twice recrystallized from hot methanol (2 mL) over 24 h in an explosion proof freezer. The solution was decanted by pipette and the crystals were rinsed with ice-cold diethyl ether (3×2 mL) to afford 2-Acetamido-2-deoxy-1,3,4,6-tetra-O-acetyl-β-D-glucopyranose as a white crystal solid (350.2 mg, 29%). $^1$H-NMR (400 MHz, CDCl$_3$): δ 5.69 (d, J=8.8 Hz, 1H), 5.41 (d, J=9.6 Hz, 1H), 5.17-5.09 (m, 2H), 4.33-4.25 (m, 2H), 4.13 (dd, J=2.4, 12.6 Hz, 1H), 3.78 (ddd, J=2.4, 4.4, 9.6 Hz, 1H), 2.12 (s, 3H), 2.09 (s, 3H), 2.05 (s, 3H), 2.04 (s, 3H). Note: Commercially available through Alfa Aesar (Cat. No.=L09020). See Knapp et al., 2009, Organic Synthesis 84:68-76.

2,3-Dihydrooxazole-3,4,6-tri-O-acetyl-β-D-glueopyranoside

2-Acetamido-2-deoxy-1,3,4,6-tetra-O-acetyl-β-D-glucopyranose (299 mg, 0.768 mmol) was dissolved in dichloroethane (21.3 mL, 0.036 M) in a 100 mL round bottom flask and then trimethylsilyl trifluoromethanesulfonate (TMSOTf, 0.149 mL, 0.806 mmol, 1.05 eq) was added. The mixture was stirred at 50° C. for 55 min after which TLC (100% EtOAc) indicated full conversion. The mixture was then removed from the heat and triethylamine (0.327 mL, 2.30 mmol, 3 eq) was added. The mixture was then stirred at room temperature for 10 min and then passed through a short plug of silica which was washed carefully with dichloromethane (25 mL) and EtOAc (15 mL). The solvent was removed under reduced pressure and the crude orange oil was purified by flash chromatography with 100% EtOAc (the column was based washed with 1% triethylamine in EtOAc prior to use) giving 2,3-Dihydrooxazole-3,4,6-tri-O-acetyl-β-D-glucopyranoside (238.2 mg, 94%) as a colorless oil. $^1$H-NMR (500 MHz, CDCl$_3$): δ 5.96 (d, J=7.5 Hz, 1H), 5.25 (app. t, J=2.5 Hz, 1H), 4.92 (dq, J=1.5, 9.3 Hz, 1H), 4.17-4.11 (m, 3H), 3.61-3.56 (m, 1H), 2.10 (s, 3H), 2.09 (s, 3H), 2.08 (d, J=2 Hz, 3H), 2.07 (s, 3H). $^{13}$C-NMR (100 MHz, CDCl$_3$): δ 170.6, 169.5, 169.2, 166.7, 99.4, 70.4, 68.4, 67.5, 65.0, 63.3, 20.9, 20.8, 20.7, 14.0. See Norberg et al., 2011, Analytical Chem. 83:1000-1007.

Isopropyl 3,4,6-tri-O-acetyl-2-(acetylamino)-2-deoxyhexopyranoside 2,3-Dihydrooxazole-3,4,6-tri-O-acetyl-β-D-glucopyranoside (0.140 g, 0.424 mmol) and anhydrous CuCl$_2$ (57 mg, 0.424 mmol, 1 eq) were coevaporated with toluene (Note: some material was lost due to the mixture bumping on the rotovap and this is reflected in the yield). Anhydrous chloroform (0.80 mL, 0.53 M) and anhydrous 2-propanol (0.13 mL, 1.72 mmol, 4.05 eq) were added to the sugar and CuCl$_2$ in a 5 mL conical sealed vessel under argon atmosphere and the reaction mixture was heated at 62° C. for 2.25 hr. After cooling to room temperature, the mixture was diluted with acetone (15 mL) and saturated aqueous sodium bicarbonate (7 mL) and the precipitated copper carbonate salts were removed by filtration through a short plug of celite which was washed with acetone (20 mL). The filtrate was removed and the residue coevaporated with toluene to remove residual water. The remainder was shaken with chloroform and weakly acidic ion-exchange resin (Amberlite IRC-86, ea 1.5 g) in order to remove remaining sugar-oxazoline starting material. Filtration, evaporation and flash chromatography (hexane/ethyl acetate, 1:3, Rf=0.24) gave isopropyl 3,4,6-tri-O-acetyl-2-(acetylamino)-2-deoxyhexopyranoside (80.3 mg, 49%) as a white solid. $^1$H-NMR (400 MHz, CDCl$_3$): δ 5.57 (d, J=8.0 Hz, 1H), 5.40 (dd, J=9.6, 10.4 Hz, 1H), 5.02, (app. t, J=9.6 Hz, 1H), 4.83 (d, J=8.0 Hz, 1H), 4.24 (dd, J=4.8, 12.2 Hz, 1H), 4.11 (dd, 2.4, 12.0 Hz, 1H), 3.92 (sept, J=6 Hz, 1H), 3.73-3.61 (m, 2H), 2.07 (s, 3H), 2.02 (s, 3H), 2.01 (s, 3H), 1.93 (s, 3H), 1.22 (d, J=6.4 Hz, 3H), 1.13 (d, J=6.0 Hz, 3H). $^{13}$C-NMR (100 MHz, CDCl$_3$): δ 170.7, 170.7, 170.2, 169.5, 99.18, 72.6, 72.2, 71.6, 69.0, 62.4, 55.6, 23.3, 23.3, 22.0, 20.7, 20.7, 20.6. HRMS (+ESI-TOF) calcd for C$_{17}$H$_{27}$NO$_9$Na [M+Na]$^+$: 412.1584. Found: 412.1555. See Wittmann et al., 2002, Eur. J. Org. Chem. 8:1363-1367.

Various publications are cited herein, the contents of which are hereby incorporated by reference in their entireties.

We claim:

1. A method of treating an infectious or inflammatory disorder comprising administering, to a subject in need of such treatment, an effective amount of a Toll-like receptor 4 inhibitor compound that is a derivative of isopropyl 3,4,6-tri-O-acetyl-2-(acetylamino)-2-deoxyhexopyranoside that reduces one or more sign or symptom of inflammation in the subject.

2. The method of claim 1, where the subject is suffering from sepsis.

3. The method of claim 1, where the subject is suffering from arthritis.

4. A method of treating an intestinal inflammatory disorder in a subject comprising administering, to a subject in need of such treatment, an effective amount of a Toll-like receptor 4 inhibitor compound that is a derivative of isopropyl 3,4,6-tri-O-acetyl-2-(acetylamino)-2-deoxyhexopyranoside that reduces intestinal inflammation in the subject.

5. The method of claim 4, where the subject is suffering from necrotizing enterocolitis.

6. The method of claim 4, where the subject is suffering from ulcerative colitis.

7. The method of claim 4, where the subject is suffering from Crohn's disease.

8. A method of treating a cardiovascular disease in a subject comprising administering, to a subject in need of such treatment, an effective amount of a Toll-like receptor 4 inhibitor compound that is a derivative of isopropyl 3,4,6-tri-O-acetyl-2-(acetylamino)-2-deoxyhexopyranoside that reduces myocardial ischemia in the subject.

9. The method of claim 8, where the subject is suffering from angina.

10. The method of claim 8, where the subject has suffered a myocardial infarction.

11. The method of claim 8, where the subject is at increased risk of suffering a myocardial infarction.

12. A method of treating a traumatic injury in a subject comprising administering, to a subject in need of such treatment, an effective amount of a Toll-like receptor 4 inhibitor compound that is a derivative of isopropyl 3,4,6-tri-O-acetyl-2-(acetylamino)-2-deoxyhexopyranoside that reduces Toll-like receptor 4-induced post-traumatic injury.

13. The method of claim 12, where the traumatic injury is to an organ selected from the group consisting of the heart, the liver, the lung, the kidney, the intestine, the brain, the eye and the pancreas.

* * * * *

UNITED STATES PATENT AND TRADEMARK OFFICE
CERTIFICATE OF CORRECTION

PATENT NO. : 9,532,999 B2  
APPLICATION NO. : 14/717349  
DATED : January 3, 2017  
INVENTOR(S) : Peter Wipf et al.

Page 1 of 1

It is certified that error appears in the above-identified patent and that said Letters Patent is hereby corrected as shown below:

On the Title Page

At item (72) Inventors:  
"Sodhi P. Chhinder"  
Should read:  
-- Chhinder P. Sodhi --

Signed and Sealed this  
Seventh Day of April, 2020

Andrei Iancu  
*Director of the United States Patent and Trademark Office*